United States Patent
Pullagurla et al.

(10) Patent No.: US 11,149,041 B2
(45) Date of Patent: Oct. 19, 2021

(54) PROCESS FOR THE PREPARATION OF GADOLINIUM COMPLEX OF (4S)-4-(4-ETHOXYBENZYL)-3,6,9-TRIS (CARBOXYLATOMETHYL)-3,6,9-TRIAZAUNDECANEDIOIC ACID DISODIUM (GADOXETATE DISODIUM)

(71) Applicant: Biophore India Pharmaceuticals PVT. Ltd., Hyderabad (IN)

(72) Inventors: Manik Reddy Pullagurla, Hyderabad (IN); Bhaskar Reddy Pitta, Hyderabad (IN); Suresh Babu Namani, Hyderabad (IN); Jagadeesh Babu Rangisetty, Hyderabad (IN)

(73) Assignee: Biophore India Pharmaceuticals PVT. Ltd., Hyderabad (IN)

( * ) Notice: Subject to any disclaimer, the term of this patent is extended or adjusted under 35 U.S.C. 154(b) by 53 days.

(21) Appl. No.: 16/305,875

(22) PCT Filed: May 30, 2017

(86) PCT No.: PCT/IN2017/050209
§ 371 (c)(1),
(2) Date: Nov. 29, 2018

(87) PCT Pub. No.: WO2017/208258
PCT Pub. Date: Dec. 7, 2017

(65) Prior Publication Data
US 2020/0123178 A1    Apr. 23, 2020

(30) Foreign Application Priority Data
May 30, 2016    (IN) .............................. 201641018460

(51) Int. Cl.
| | | |
|---|---|---|
| *C07F 5/00* | (2006.01) | |
| *C07C 213/02* | (2006.01) | |
| *C07C 227/02* | (2006.01) | |
| *C07C 227/18* | (2006.01) | |
| *C07C 269/04* | (2006.01) | |
| *C07C 269/06* | (2006.01) | |
| *C07C 271/02* | (2006.01) | |
| *C07C 303/04* | (2006.01) | |
| *C07C 309/24* | (2006.01) | |

(52) U.S. Cl.
CPC ............ *C07F 5/003* (2013.01); *C07C 213/02* (2013.01); *C07C 227/02* (2013.01); *C07C 227/18* (2013.01); *C07C 269/04* (2013.01); *C07C 269/06* (2013.01); *C07C 271/02* (2013.01); *C07C 303/04* (2013.01); *C07C 309/24* (2013.01)

(58) Field of Classification Search
None
See application file for complete search history.

(56) References Cited

FOREIGN PATENT DOCUMENTS

| | | |
|---|---|---|
| CN | 101007775 A | 8/2007 |
| CN | 103420862 A | 12/2013 |
| CN | 103864630 B | 7/2015 |
| CN | 104761461 A | 7/2015 |
| WO | WO2011154333 A2 | 12/2011 |

OTHER PUBLICATIONS

Schmitt-Willich et al. Synthesis and Physicochemical Characterization of a New Gadolinium Chelate: The Liver-Specific Magnetic Resonance Imaging Contrast Agent Gd-EOB-DTPA. 1999 Inorg. Chem. 38: 1134-1144. (Year: 1999).*

* cited by examiner

*Primary Examiner* — Jennifer Lamberski
(74) *Attorney, Agent, or Firm* — Ling Wu; Stephen Yang; Ling and Yang Intellectual Property

(57) ABSTRACT

The present invention discloses a novel process for the preparation of gadolinium complex of (4S)-4-(4-Ethoxybenzyl)-3,6,9-tris(carboxylatomethyl)-3,6,9-triazaundecanedioic acid disodium of formula 1 and novel intermediates thereof.

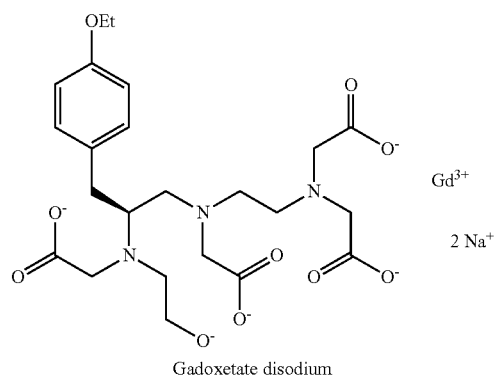

Gadoxetate disodium

Formula 1

12 Claims, 1 Drawing Sheet

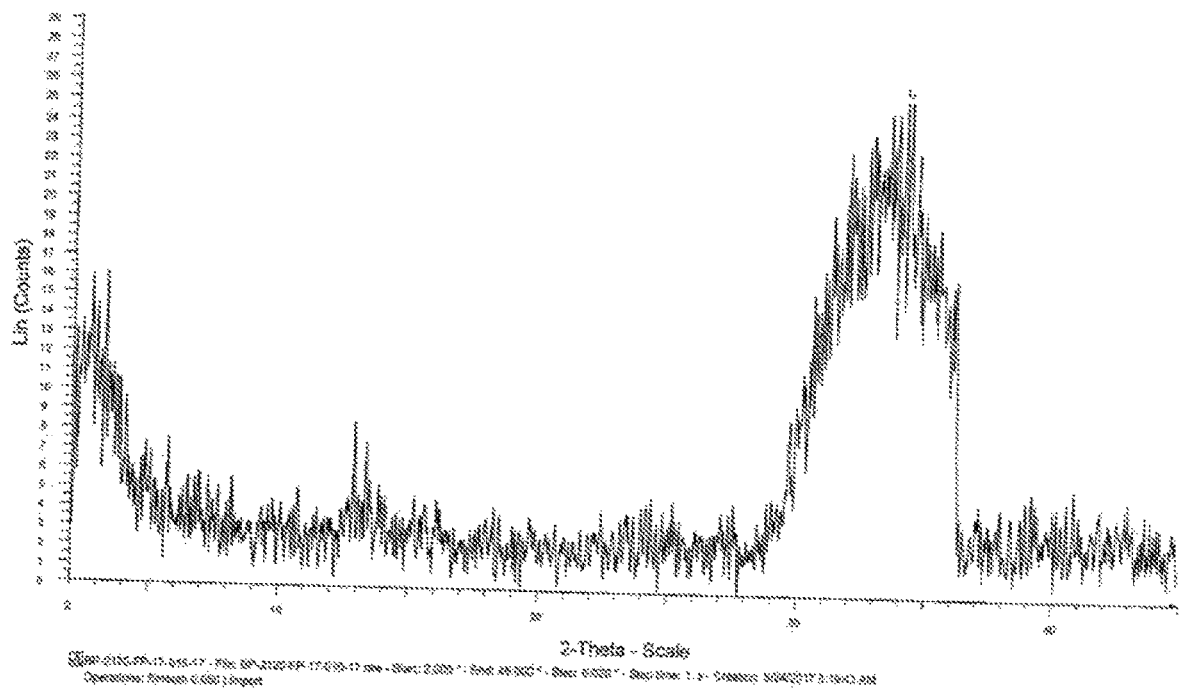
Characteristic X-Ray diffractogram of Gadoxetate disodium (1)

PROCESS FOR THE PREPARATION OF GADOLINIUM COMPLEX OF (4S)-4-(4-ETHOXYBENZYL)-3,6,9-TRIS (CARBOXYLATOMETHYL)-3,6,9-TRIAZAUNDECANEDIOIC ACID DISODIUM (GADOXETATE DISODIUM)

FIELD OF THE INVENTION

The present invention relates to a novel process for the preparation of gadolinium complex of (4 S)-4-(4-Ethoxybenzyl)-3,6,9-tris(carboxylatomethyl)-3,6,9-triazaundecanedioic aciddisodium of formula 1 and its novel intermediates thereof.

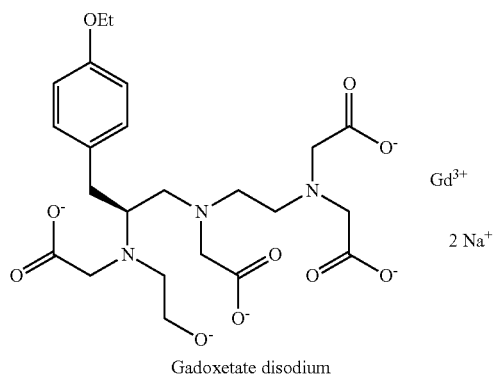

Gadoxetate disodium

BACKGROUND OF THE INVENTION

Gadoxetate disodium of formula 1 is chemically known as (4S)-4-(4-Ethoxybenzyl)-3,6,9-tris(carboxylatomethyl)-3,6,9-triazaundecanedioic acid, gadolinium complex, disodium salt. The structural formula of Gadoxetate disodium in aqueous solution is represented as follows.

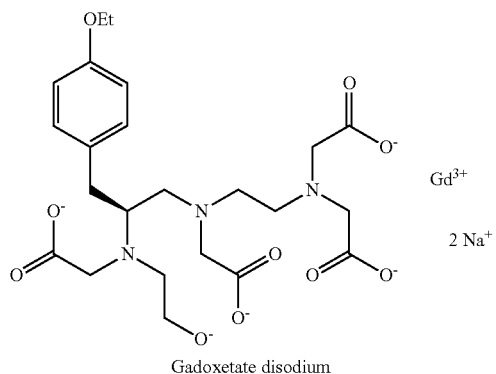

Gadoxetate disodium

Gadoxetate disodium is a gadolinium-based MRI contrast agent. It is marketed as Primovist in Europe and Eovist in the United States by Bayer HealthCare pharmaceutics. It is a hepatospecific paramagnetic gadolinium-based contrast agent used exclusively in MRI liver imaging.

The following patents and applications describe various synthetic methods of Gadoxetate disodium.

The compound of formula 1 was first reported in U.S. Pat. No. 5,798,092, which describes synthesis of formula 1 by ethylation of intermediate 2 with iodoethane in the presence of sodium hydride to obtain penta-tert-butyl ester of compound 3 followed by de-protection of tert-butyl group of compound 3 with trifluoro acetic acidto get compound 4. Subsequent complexation of chelate 4 with gadolinium(III) oxide ($Gd_2O_3$) has given Gadoxetate disodium as shown in scheme-1.

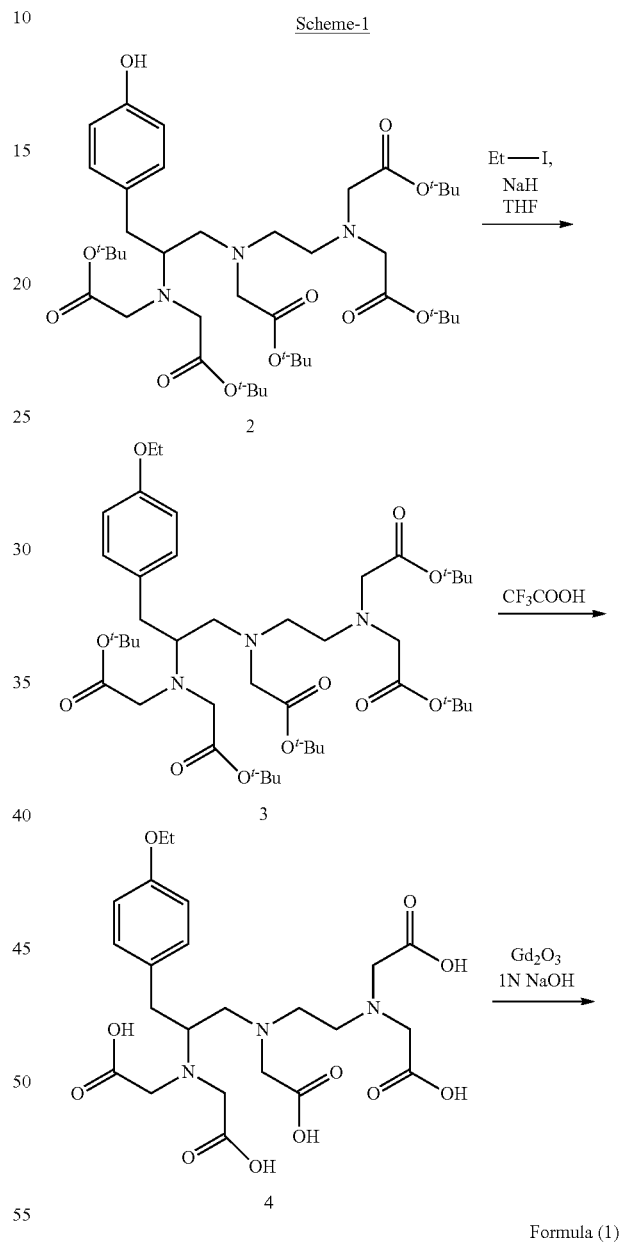

Formula (1)

In this process compound 3 requires chromatographic purification after ethylation of compound 2. Finally, sodium salt i.e., formula (1) can be obtained by freeze drying, which makes the process expensive and impractical at a commercial scale production.

In turn, the synthesis of the intermediate 2, was reported in U.S. Pat. No. 5,482,700, which describes multi-step synthesis from the O-benzyl tyrosine 5 as illustrated in Scheme-2. The synthesis of compound 2 requires six steps with expensive and complex reagents such as Pd/C, diborane ($B_2H_6$) and volatile and unstable iodoethane. Synthesis of compound 11 is practically very difficult and quenching of diborane is tedious. In addition, it requires additional steps for the synthesis of compound 5 and compound 7.

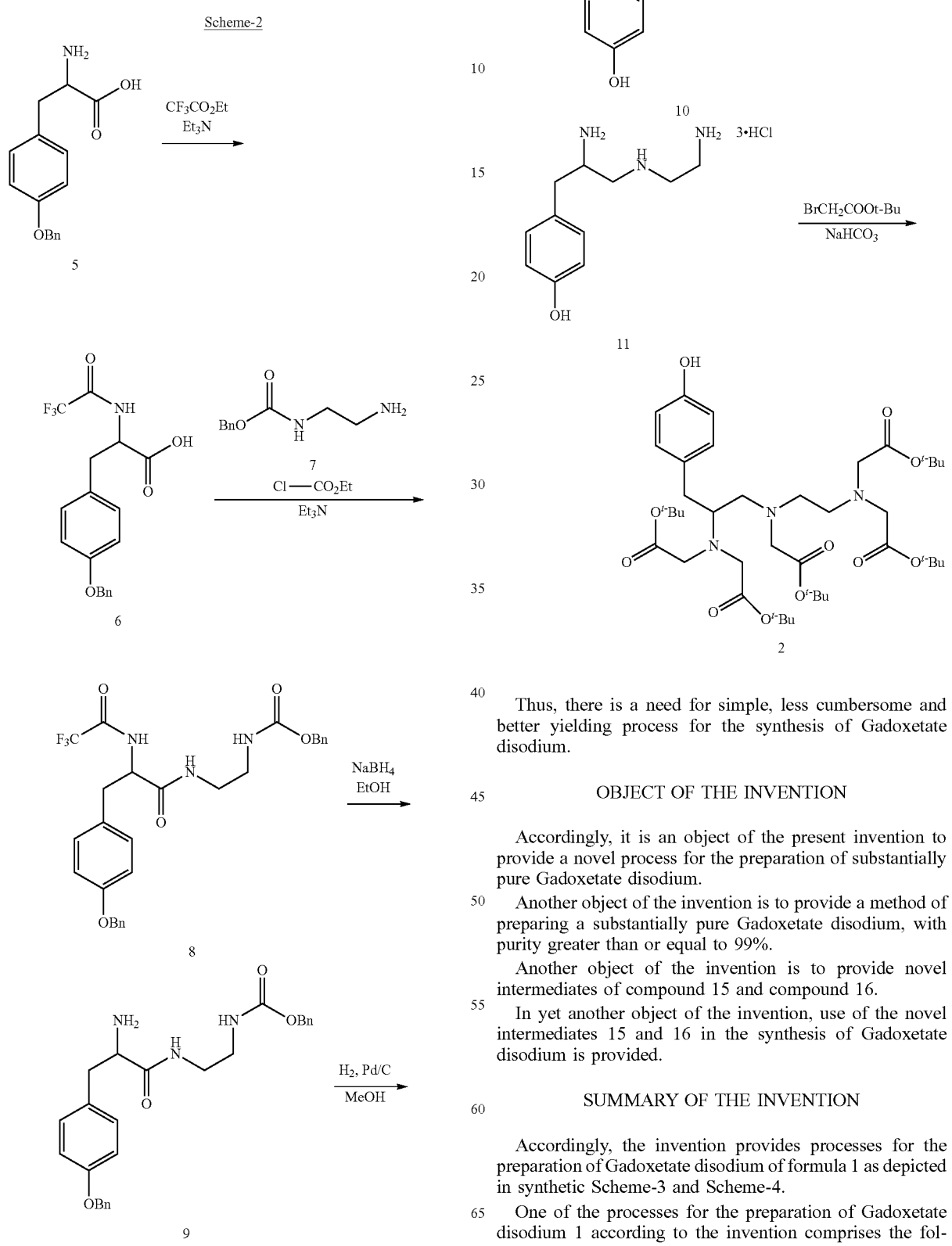

Thus, there is a need for simple, less cumbersome and better yielding process for the synthesis of Gadoxetate disodium.

OBJECT OF THE INVENTION

Accordingly, it is an object of the present invention to provide a novel process for the preparation of substantially pure Gadoxetate disodium.

Another object of the invention is to provide a method of preparing a substantially pure Gadoxetate disodium, with purity greater than or equal to 99%.

Another object of the invention is to provide novel intermediates of compound 15 and compound 16.

In yet another object of the invention, use of the novel intermediates 15 and 16 in the synthesis of Gadoxetate disodium is provided.

SUMMARY OF THE INVENTION

Accordingly, the invention provides processes for the preparation of Gadoxetate disodium of formula 1 as depicted in synthetic Scheme-3 and Scheme-4.

One of the processes for the preparation of Gadoxetate disodium 1 according to the invention comprises the following steps as described in Scheme-3.

Scheme 3

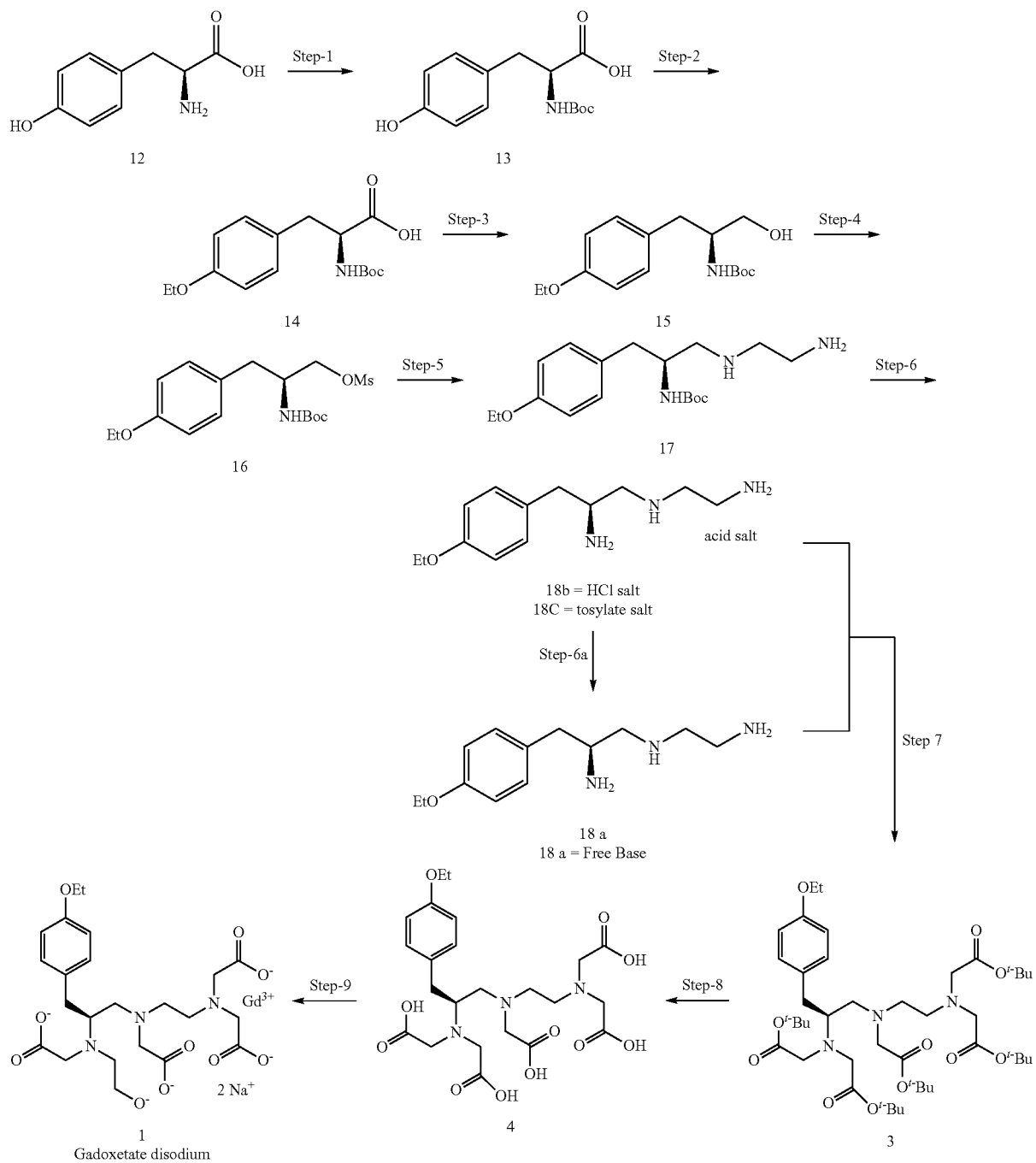

1) First step of the synthetic scheme-3 involves protection of amino group of L-tyrosine of formula 12 with di-tert-butyl dicarbonate ($Boc_2O$) in presence of base to get boc-protected L-tyrosine of formula 13;
2) The second step involves alkylation of boc-protected L-tyrosine of formula 13 with diethyl sulfate in a suitable solvent to obtain compound of formula 14;
3) Reduction of compound of formula 14 by reacting with ethyl chloroformate or methyl iodide to generate in situ the corresponding anhydride or ester followed by treating with suitable reducing agent to obtain (S)-tert-butyl (1-(4-ethoxyphenyl)-3-hydroxypropan-2-yl)carbamate of formula 15;
4) Protection of hydroxyl group in (S)-tert-butyl(1-(4-ethoxyphenyl)-3-hydroxypropan-2-yl)carbamate 15 with methane sulfonyl chloride in presence of base to obtain (S)-2-((tert-butoxycarbonyl)amino)-3-(4-ethoxyphenyl)propyl methanesulfonate of formula 16.
5) Condensation of (S)-2-((tert-butoxycarbonyl)amino)-3-(4-ethoxyphenyl)propyl methanesulfonate of formula 16 with ethylenediamine in a suitable solvent to obtain (S)-tert-butyl(1-((2-aminoethyl)amino)-3-(4-ethoxyphenyl)propan-2-yl)carbamate of formula 17;
6) Deprotection of Boc-group in (S)-tert-butyl (1-((2-aminoethyl)amino)-3-(4-ethoxyphenyl)propan-2-yl) carbamate in presence of suitable acid to obtain (S)—N1-(2-aminoethyl)-3-(4-ethoxyphenyl)propane-1,2-diamine acid salt of formula 18, optionally, is further converted in to free base of formula 18a in situ by reaction with a suitable base;
7) Alkylation of (S)—N1-(2-aminoethyl)-3-(4-ethoxyphenyl)propane-1,2-diamine salt or free base with tert-butyl bromoacetate in presence of potassium carbonate to provide (S)-tert-butyl 2,2'-(2-((2-(bis(2-tert-butoxy-2-oxoethyl)amino)-3-(4-ethoxyphenyl)propyl) (2-tert-butoxy-2-oxoethyl)amino)ethylazanediyl)diacetate of formula 3;
8) Deprotection of tertiary butylgroup of (S)-tert-butyl 2,2'-(2-((2-(bis(2-tert-butoxy-2-oxoethyl)amino)-3-(4-ethoxyphenyl)propyl) (2-tert-butoxy-2-oxoethyl)amino)ethylazanediyl)diacetate of formula 3 with aqueous sodium hydroxide to obtain (S)-2,2'-((2-((2-(bis(carboxymethyl)amino)-3-(4-ethoxyphenyl)propyl)(carboxymethyl)amino)ethyl)azanediyl)diacetic acid of formula 4;
9) Final step involves treating (S)-2,2'-((2-((2-(bis(carboxymethyl)amino)-3-(4-ethoxyphenyl)propyl)(carboxymethyl)amino)ethyl)azanediyl)diacetic acid of formula 4 with Gadolinium(III) oxide in presence of a suitable base to obtain Gadoxetate disodium of formula 1.

Optionally alkylation of (S)—N1-(2-aminoethyl)-3-(4-ethoxyphenyl)propane-1,2-diamine acid salt 18 or free base 18a with tertiary butyl bromoacetate in presence of base can be performed by using phase transfer catalyst tertiary butyl ammonium bromide and the product so obtained in this step is directly converted into next stage without any purification to obtain formula 4, which is purified from a mixture of protic solvents. The resulting intermediate 4 is subsequently converted into Gadoxetate disodium of formula 1 by treatment with gadolinium dioxide.

In another embodiment of the invention Gadoxetate disodium is synthesized by the reaction as depicted in Scheme-4.

Scheme 4

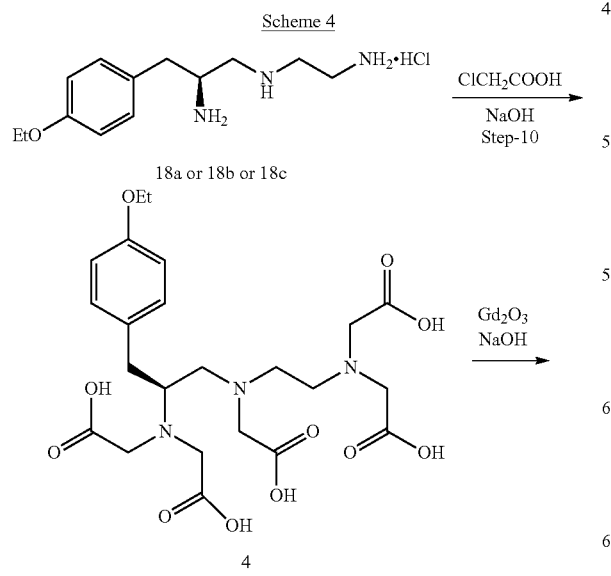

In the second process the intermediates 18b or 18c or 18a are subjected to alkylation using chloroacetic acid or bromoacetic acid in the presence of suitable base followed by purification from a mixture of protic solvents and the resulting intermediate 4 is subsequently converted into Gadoxetate disodium of formula 1 by treatment with gadolinium dioxide.

The intermediate 4 produced according to Scheme-3 and Scheme-4 is having purity greater than 99%.

Thus in one embodiment the invention provides a process for the preparation of gadolinium complex of (4S)-4-(4-Ethoxybenzyl)-3,6,9-tris(carboxylatomethyl)-3,6,9-triazaundecanedioic acid disodium (Gadoxetate disodium) of formula 1 comprising the steps of:

i) protecting amino group of L-tyrosine of formula 12 with di-tert-butyl dicarbonate (Boc₂O) in presence of base to get boc-protected L-tyrosine of formula 13;

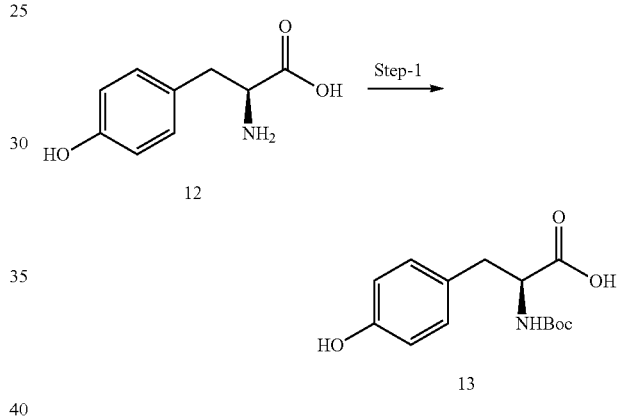

ii) alkylating Boc-protected L-tyrosine of formula 13 with diethyl sulfate in a suitable solvent to obtain formula 14;

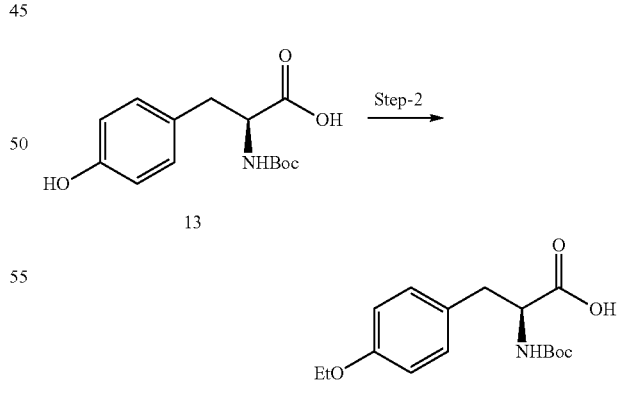

iii) converting formula 14 in to anhydride or ester in situ by reacting with suitable reagent followed by reduction with reducing agent to obtain (S)-tert-butyl(1-(4-ethoxyphenyl)-3-hydroxypropan-2-yl)carbamate of formula 15;

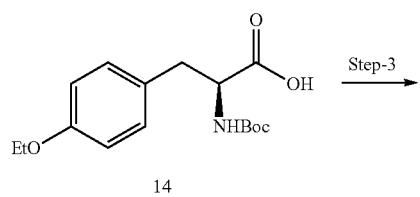

14

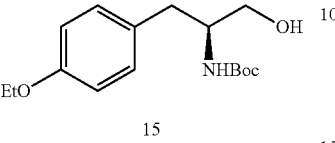

15 iv) protecting hydroxyl group in (S)-tert-butyl(1-(4-ethoxyphenyl)-3-hydroxypropan-2-yl)carbamate with methanesulfonyl chloride in presence of base to obtain (S)-2-((tert-butoxycarbonyl)amino)-3-(4-ethoxyphenyl)propyl methanesulfonate of formula 16;

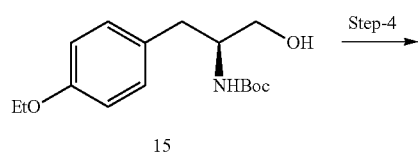

15

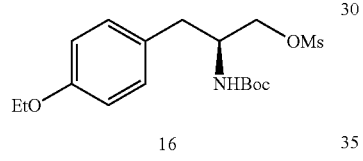

16 v) condensing (S)-2-((tert-butoxy carbonyl)amino)-3-(4-ethoxyphenyl)propylmethane sulfonate of formula 16 with ethylenediamine in a suitable solvent to obtain (S)-tert-butyl(1-((2-aminoethyl)amino)-3-(4-ethoxyphenyl)propan-2-yl)carbamate of formula 17;

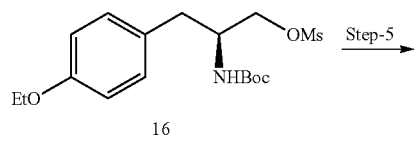

16

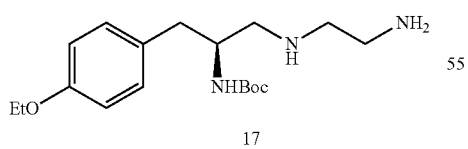

17 vi) deprotecting amino protecting from (S)-tert-butyl (1-((2-aminoethyl)amino)-3-(4-ethoxyphenyl)propan-2-yl)carbamate using suitable acid to obtain (S)—N1-(2-aminoethyl)-3-(4-ethoxyphenyl)propane-1,2-diamine acid salt of formula 18, which is further converted in to free base of formula 18a in situ optionally, by reaction with a suitable base;

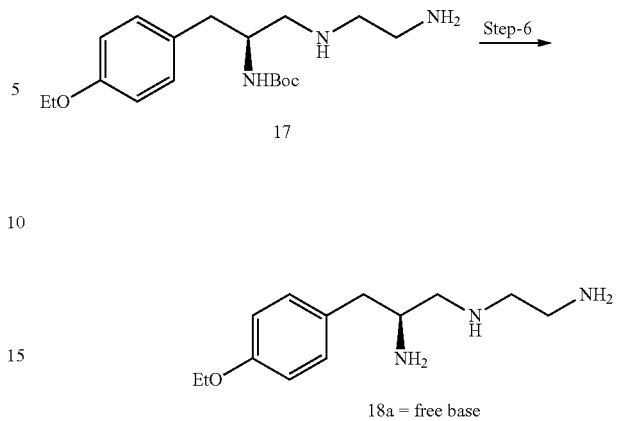

18a = free base
18b = HCl salt
18c = tosylaye salt vii) alkylating (S)—N1-(2-aminoethyl)-3-(4-ethoxyphenyl)propane-1,2-diamine acid salt or free base with tertiary butyl bromoacetate in presence of potassium carbonate to provide (S)-tert-butyl 2,2'-(2-((2-(bis(2-tert-butoxy-2-oxoethyl) amino)-3-(4-ethoxyphenyl) propyl) (2-tert-butoxy-2-oxoethyl)amino)ethyl azanediyl)diacetate of formula 3;

18a = free base,
18b = HCl salt,
18c = tosylaye salt

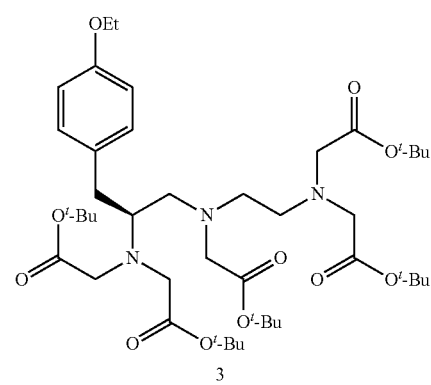

3 viii) deprotecting tertiary butyl group of (S)-tert-butyl 2,2'-(2-((2-(bis(2-tert-butoxy-2-oxoethyl)amino)-3-(4-ethoxyphenyl)propyl) (2-tert-butoxy-2-oxoethyl) amino)ethyl azanediyl)diacetate of formula 3 with aqueous sodium hydroxide to obtain (S)-2,2'-((2-((2-(bis(carboxymethyl)amino)-3-(4-ethoxyphenyl)propyl) (carboxymethyl)amino)ethyl)azanediyl)diacetic acid of formula 4;

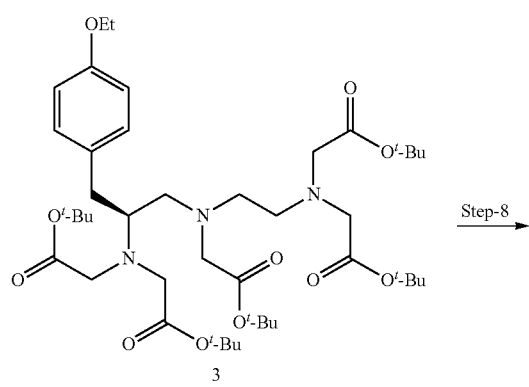

Step-8

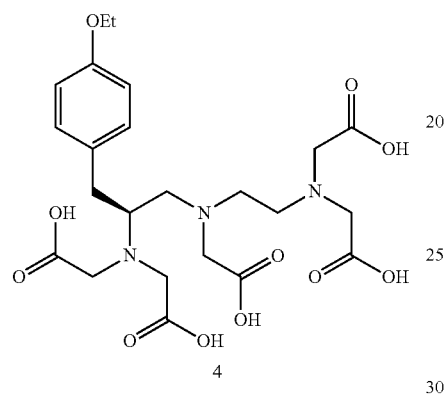

4 ix) converting (S)-2,2'-((2-((2-(bis(carboxymethylamino)-3-(4-ethoxyphenyl)propyl) (carboxymethyl) amino)ethyl)azanediyl)diacetic acid of formula 4 to Gadolinium salt by treating with Gadolinium(III) oxide in presence of sodium hydroxide.

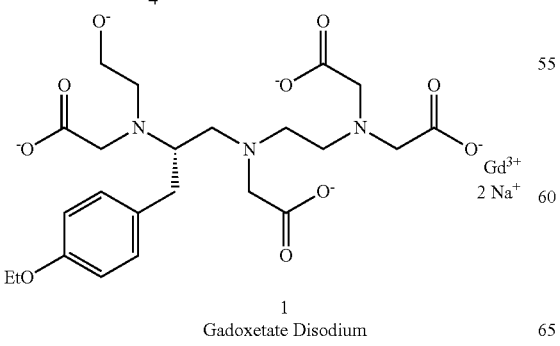

Step-9

1
Gadoxetate Disodium

The reducing agent of step-iii is selected from the group comprising of sodium cyanoborohydride, sodium triacetoxy boron hydride, lithium aluminium hydride and sodium borohydride. In one embodiment the reducing agent used is sodium borohydride.

The hydroxyl protecting group of step-iv is selected from the group comprising of mesylates, tosylates, acetates and triflates. In one embodiment the hydroxyl protecting agent used is methanesulfonyl chloride.

The amino deprotecting reaction of step-vi is carried out in presence of p-toluene sulphonic acid or hydrochloric acid.

In another embodiment the invention provides a process for preparation of Gadoxetate disodium of formula 1 comprising the steps of:

a) alkylating compound of formula 18b or 18c or 18a using halo acetic acid in presence of sodium hydroxide to obtain intermediate of formula 4;

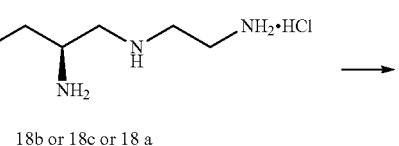

18b or 18c or 18 a

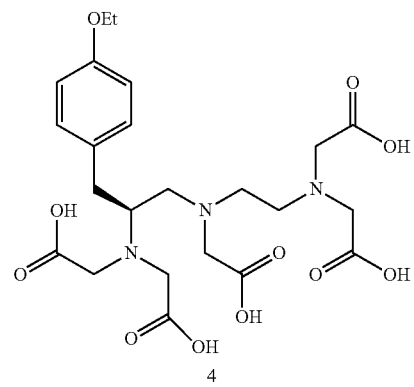

4 b) treating (S)-2,2'-((2-((2-(bis(carboxymethyl)amino)-3-(4-ethoxyphenyl)propyl) (carboxymethyl)amino)ethyl) azanediyl)diacetic acid of formula 4 with Gadolinium (III) oxide in presence water and sodium hydroxide to obtain Gadoxetate disodium of formula 1.

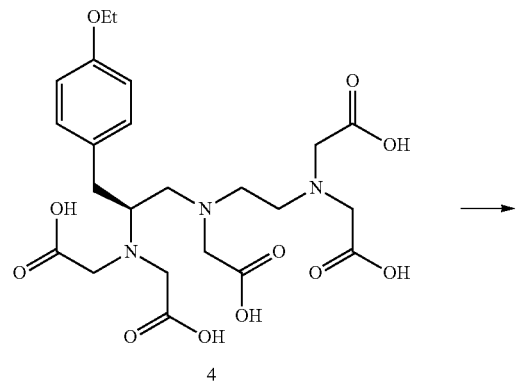

4

-continued

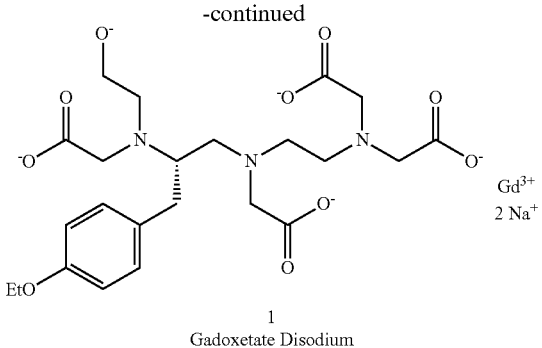

1
Gadoxetate Disodium

The halo acetic acid used is selected from the group comprising of bromoacetic acid, chloro acetic acid and iodoacetic acid.

In another embodiment the invention provides a process for preparation of Gadoxetate disodium of formula 1 with greater than 99% purity comprising the steps of:
a) suspending compound of formula 4 in water and adjusting pH of the solution to 3.0 to 3.2 using acid resin;

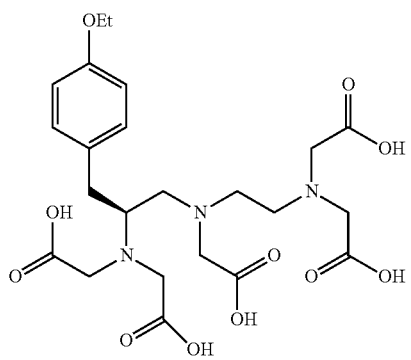

4 b) removing the resin and adding gadolinium oxide to the reaction mixture;
c) heating the reaction mixture for 4-5 hrs. at 85-90° C.;
d) filtering and adjusting pH to 6.5 to 7.0 using base;
e) treating with activated carbon at 40-45° C. and filtering through hyflo bed.

In the above process the acid resin used is selected from INDION 225H and 525H.

The base used is selected from the group comprising of potassium hydroxide, lithium hydroxide, sodium hydroxide, potassium carbonate and sodium carbonate.

In another aspect the invention provides novel intermediate compounds of formula 15 and formula 16, which are used in the synthesis of Gadoxetate disodium of formula 1.

In one embodiment the invention provides a compound (S)-tert-butyl 1-(4-ethoxyphenyl)-3-hydroxypropan-2-ylcarbamate of formula 15.

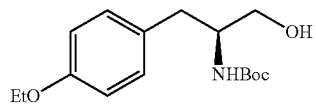

15

In one embodiment the invention provides a compound (S)-2-((tert-butoxycarbonyl)amino)-3-(4-ethoxyphenyl) propyl methanesulfonate of formula 16.

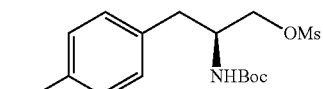

16

In another aspect the invention provides a process for the preparation of (S)-2,2'-(2-((2-(bis(carboxymethyl)amino)-3-(4-ethoxyphenyl)propyl)(carboxymethyl)amino)ethyl-azanediyl)diacetic acid of formula 4

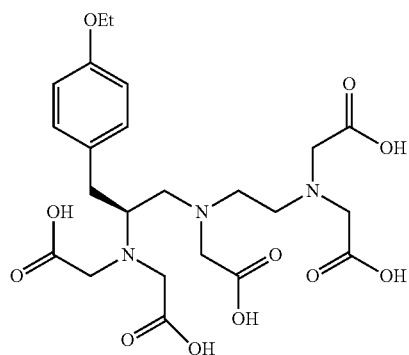

4 with greater than 99% purity comprising the steps of:
i. suspending compound 3 in methanol and aqueous sodium hydroxide;

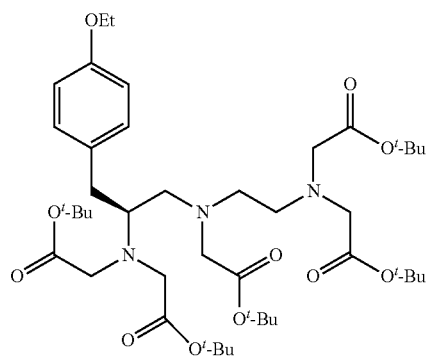

3 ii. refluxing the solution for 5-6 hrs;
iii. cooling to room temperature and adjusting pH to 6.5 to 7.0 by acidic resin;
iv. filtering and washing the solid with a mixture of methanol and isopropyl alcohol.

Where not defined in above reaction steps, the below definitions of terms define alkylation reagent, hydroxyl activating groups, organic base, base, aprotic solvent, protic solvent, alcoholic solvent, etc.

The term "alkylation reagent" used herein is selected from the group comprising of diethyl sulphate, ethyl iodide, ethyl bromide, ethyl chloride or the like.

The term "hydroxyl activating groups' used herein is selected from the group comprising of mesylates, tosylates, acetates, triflates or the like, most preferably methanesulfonyl chloride.

The term "organic base" used herein is selected from the group comprising pyridine, triethylamine, leutidine, 1,4-diazabicyclo[2.2.2]octane (DABCO), 1,8-Diazabicyclo[5.4.0]undec-7-ene (DBU), 1,2,2,6,6-pentamethylpipiridine, 1,1,3,3-tetramethylguanidine, N,N-Diisopropylethylamine (iPr$_2$Net), tri n-butyl amine (NBu$_3$), N,N-Dicyclohexylmethylamine (Cy$_2$NMe) or the like, most preferably triethylamine.

The term "base" used herein is selected from the group comprising of alkali hydroxides, alkoxides, alkali hydrides, or compounds such as amine derivatives, carbonates or the like, for example potassium hydroxide, lithium hydroxide, sodium hydroxide, potassium carbonate, sodium carbonate, lithium carbonate, alkoxides like sodium methoxide, sodium ethoxides, potassium tert.butoxide, sodium tert.butoxide, organic bases such as triethyl amine, pyridine, 4-Dimethylaminopyridine (DMAP), Sodium bis(trimethylsilyl)amide (NaHMDS), lithium bis(trimethylsilyl)amide (LiHMDS), Diisopropylamine (DIPA), pyrrolidine or the like.

The term 'aprotic solvent' used herein is selected from the group comprising of dichloromethane, chloroform, dichloroethane acetonitrile, dimethyl sulphoxide (DMSO), tetrahydrofuran (THF), dimethyl formamide (DMF), ethyl acetate, acetone, n-methyl pyrrolidine (NMP), dimethyl acetamide (DMA), diethyl ether, methyl tert-butyl ether (MTBE), toluene, cyclohexanes, hexanes, dioxanes or the like.

The term 'protic solvent' used herein is selected from the group comprising of alcohols like methanol, ethanol, isopropanol, n-propanol, n-butanol; water; formic acid, nitromethane, acetic acid or the like.

The term 'alcoholic solvent' used herein is selected from the group comprising of methanol, ethanol, n-propanol, n-butanol, isopropyl alcohol or the like.

The term solvent used herein is selected from the group comprising of aprotic, protic, water or mixtures thereof.

The term strong acid resin used herein is selected from the group comprising of INDION 225, 525H or the like.

BRIEF DESCRIPTION OF DRAWINGS

FIG. 1: Characteristic X-Ray powder diffractogram of Gadoxetate disodium 1

DETAILED DESCRIPTION OF THE INVENTION

The present invention relates to a novel process for the preparation of gadolinium complex of (4S)-4-(4-Ethoxybenzyl)-3,6,9-tris(carboxylatomethyl)-3,6,9-triazaundecanedioic acid disodium (Gadoxetate disodium) of formula 1 and its novel intermediates thereof.

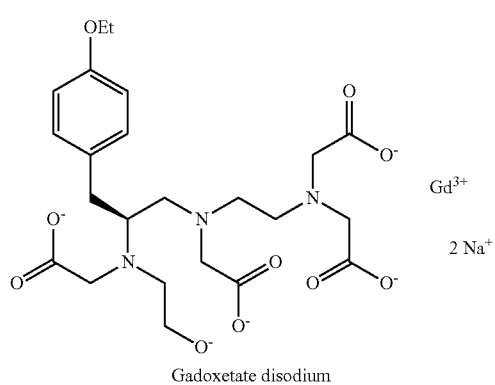

Gadoxetate disodium

Accordingly, in one aspect the invention provides processes for the preparation of Gadoxetate disodium 1 involving following steps as described in below general synthetic Scheme-3.

Scheme-3

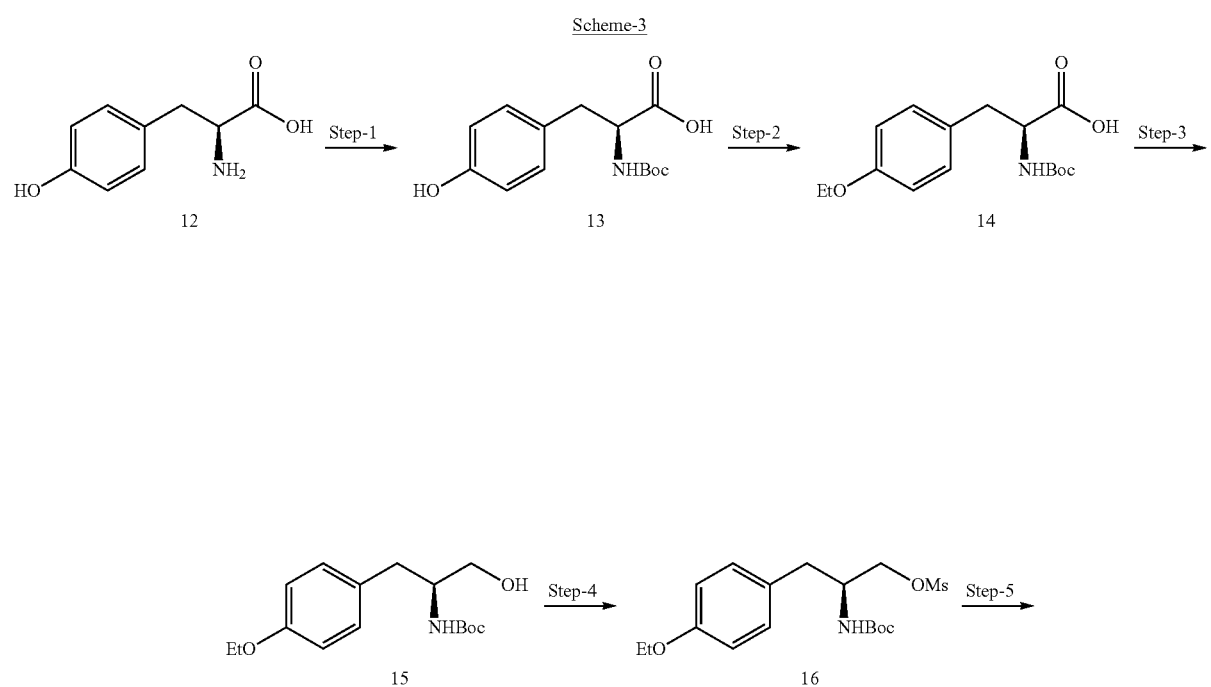

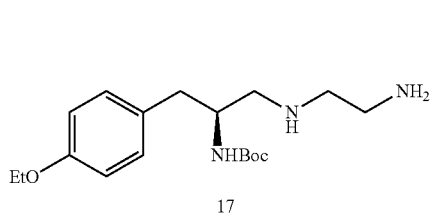

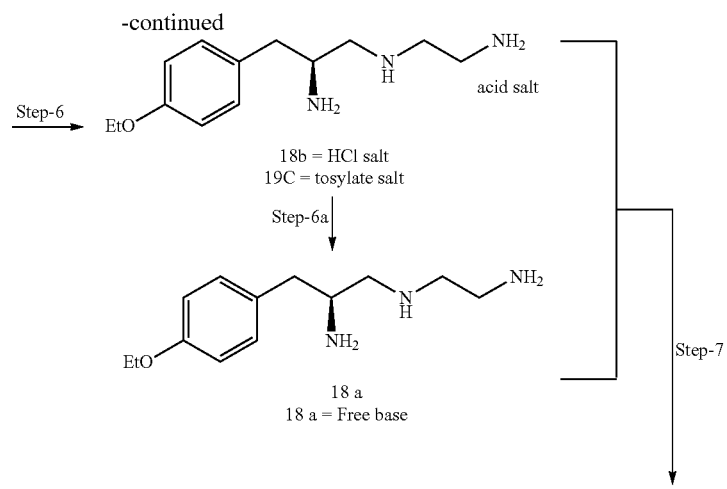

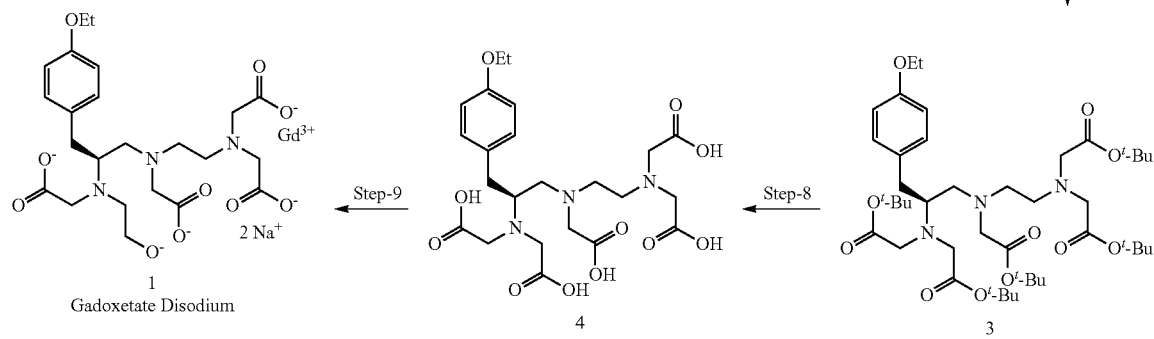

Above Scheme-3 for the preparation of Gadoxetate disodium 1 involves reaction steps 1-9 as follows:
1) First step of the synthetic scheme-3 involves protection of amino group of L-tyrosine of formula 12 with di-tert-butyl dicarbonate (Boc$_2$O) in presence of base to get boc-protected L-tyrosine of formula 13;
2) The second step involves alkylation of boc-protected L-tyrosine of formula 13 with diethyl sulfate in a suitable solvent to obtain compound of formula 14;
3) Reduction of compound of formula 14 by reacting with ethyl chloroformate or methyl iodideto generate in situ the corresponding anhydride or ester followed bytreating with suitable reducing agent to obtain (S)-tert-butyl (1-(4-ethoxyphenyl)-3-hydroxypropan-2-yl)carbamate of formula 15;
4) Protection of hydroxyl group in (S)-tert-butyl(1-(4-ethoxyphenyl)-3-hydroxypropan-2-yl)carbamate 15 with methane sulfonyl chloride in presence of base to obtain (S)-2-((tert-butoxycarbonyl)amino)-3-(4-ethoxyphenyl)propyl methanesulfonate of formula 16.
5) Condensation of (S)-2-((tert-butoxycarbonyl)amino)-3-(4-ethoxyphenyl)propyl methanesulfonate of formula 16 with ethylenediamine in a suitable solvent to obtain (S)-tert-butyl(1-((2-aminoethyl)amino)-3-(4-ethoxyphenyl)propan-2-yl)carbamate of formula 17;
6) Deprotection of Boc-group in (S)-tert-butyl (1-((2-aminoethyl)amino)-3-(4-ethoxyphenyl)propan-2-yl) carbamate in presence of suitable acid to obtain (S)—N1-(2-aminoethyl)-3-(4-ethoxyphenyl)propane-1,2-diamine acid salt of formula 18, optionally, is further converted in to free base of formula 18a in situ by reaction with a suitable base;
7) Alkylation of (S)—N1-(2-aminoethyl)-3-(4-ethoxyphenyl)propane-1,2-diamine salt or free base with tert-butyl bromoacetate in presence of potassium carbonate to provide (S)-tert-butyl 2,2'-(2-((2-(bis(2-tert-butoxy-2-oxoethyl) amino)-3-(4-ethoxyphenyl)propyl) (2-tert-butoxy-2-oxoethyl)amino)ethylazanediyl)diacetate of formula 3;
8) Deprotection of tertiary butylgroup of (S)-tert-butyl 2,2'-(2-((2-(bis(2-tert-butoxy-2-oxoethyl)amino)-3-(4-ethoxyphenyl)propyl) (2-tert-butoxy-2-oxoethyl) amino)ethylazanediyl)diacetate of formula 3 with aqueous sodium hydroxide to obtain (S)-2,2'-((2-((2-(bis(carboxymethyl)amino)-3-(4-ethoxyphenyl)propyl)(carboxymethyl)amino)ethyl)azanediyl)diacetic acid of formula 4;
9) Final step involves treating (S)-2,2'-((2-((2-(bis(carboxymethyl)amino)-3-(4-ethoxyphenyl)propyl)(carboxymethyl)amino)ethyl)azanediyl)diacetic acid of formula 4 with Gadolinium(III) oxide in presence of a suitable base to obtain Gadoxetate disodium of formula 1.

Optionally alkylation of (S)-N1-(2-aminoethyl)-3-(4-ethoxyphenyl)propane-1,2-diamine acid salt 18 or free base 18a with tertiary butyl bromoacetate in presence of base can be performed by using phase transfer catalyst tertiary butyl ammonium bromide and the product so obtained in this step is directly converted into next stage without any purification to obtain formula 4, which is purified from a mixture of protic solvents. The resulting intermediate 4 is subsequently converted into Gadoxetate disodium of formula 1 by treatment with gadolinium dioxide.

In another embodiment of the invention Gadoxetate disodium is synthesized by the reaction as depicted in Scheme-4.

Scheme-4

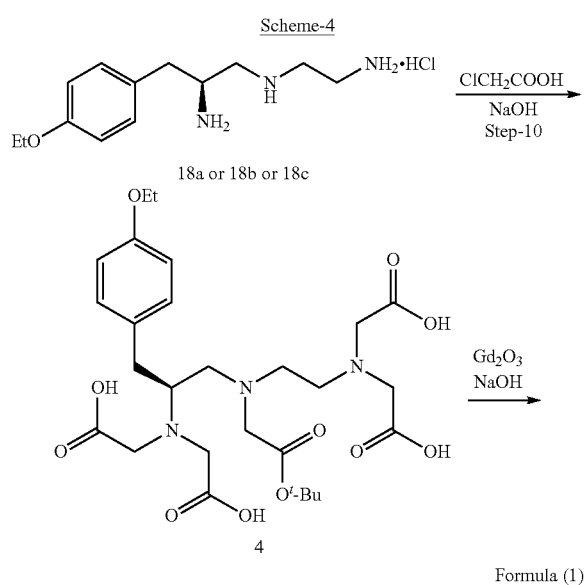

In the second process the intermediates 18b or 18c or 18a are subjected to alkylation using chloroacetic acid or bromoacetic acid in the presence of suitable base followed by purification from a mixture of protic solvents and the resulting intermediate 4 is subsequently converted into Gadoxetate disodium of formula 1 by treatment with gadolinium dioxide.

The intermediate 4 produced according to Scheme-3 and Scheme-4 is having purity greater than 99%.

Two methods for preparing Gadoxetate disodium according to the present invention are characterized by the steps of synthesizing novel intermediates 15 and 16.

According to the general method of synthesis shown in Scheme-3, the intermediate 15 is prepared from L-tyrosine 12 by reaction with di-tert-butyl dicarbonate to generate intermediate 13. The reaction is performed in the presence of suitable base i.e preferably triethylamine and the temperature ranges from −5 to 10° C. The intermediate 13 is treated with suitable alkylation reagent in the presence of suitable base to obtain compound 14. The suitable base used in step 2 is sodium hydroxide.

Intermediate 14 is treated with ethylchloroformate or methyl iodide to generate in situ the corresponding anhydride or ester in presence of suitable base and subsequent reduction with suitable reducing agent generates compound 15. The reaction temperature ranges from 10 to 25° C., preferably 15 to 25° C. The suitable base used in step-3 is selected from the group comprising of triethylamine, sodium hydroxide, potassium hydroxide, sodium carbonate, potassium carbonate or the like.

Suitable solvent used for the step-3 reaction is selected from the group comprising of dichloromethane, methanol, tetrahydrofuran or the like and mixtures thereof. The suitable reducing agents are selected from the group comprising of sodium cyanoborohydride, sodium triacetoxy boron hydride, lithium aluminium hydride, sodium borohydride or the like. The intermediate 15 obtained is further purified using suitable solvents, wherein the solvents employed are protic, aprotic or mixtures thereof, selected from the group comprising ethylacetate, n-hexane, cyclohexane or the like.

In step-4, primary hydroxyl group of compound 15 is activated with hydroxyl activating groups in the presence of suitable base. The reaction is performed at the temperature ranging from 10 to 25° C.; reaction completion time ranges from 12-24 hrs. The suitable solvent used in step-4 reaction is selected from the group comprisising of chlorosolvents, ethers and mixtures thereof. In one aspect, the obtained intermediate 16 is purified by using suitable solvent selected from protic solvents and aprotic solvents and the mixtures thereof.

The solvents used for purification of compound 16 is selected from the group comprising of ethyl acetate, n-hexane, cyclohexane, methyl tertiary butyl ether, diethyl ether, tetrahydrofuran, water or the like and mixtures thereof; most preferably the solvent used is methyl tertiary butyl ether.

Alternatively, corresponding, bromo and iodo compounds can be used as leaving groups in place of hydroxyl activating groups of intermediate 16.

In step-5, compound 16 is condensed with ethylenediamine with and without using any solvent. The quantity of ethylenediamine varies from 10-25 eq. and the reaction temperature range from room temperature to reflux; Suitable solvent used for the stage-5 reaction is selected from the group comprising of aromatic hydrocarbon solvents, amide solvents, sulphoxide solvents, ethers solvents such as of toluene, xylene, N,N-dimethylformamide, dimethylsufoxide, tetrahydrofuran, 1,4-dioxaneor the like. In one aspect, the solvent used for the reaction is tetrahydrofuran.

In step-6, deprotection of compound 17 with concentrated hydrochloric acid or p-toluene sulphonic acid in presence of suitable solvent provided hydrochloride or tosylate salt of intermediate 18 respectively. Suitable solvent used for the step-6 reaction is selected from the group comprising of 1,4-dioxane, ethyl acetate, methanol, Isopropyl alcohol or mixtures thereof.

In step-7, alkylation of free base of compound 18 or optionally its acid salt (18b or 18c) reacts with tert-Butyl bromoacetate in the presence of suitable base and aprotic solvent. Optionally step-7 can be performed in the presence of phase transfer catalyst tertiary butyl ammonium bromide and the product so obtained in this step is directly converted into next stage without any purification to obtain formula 4. Subsequently in step-8, hydrolysis of penta-tert-butyl ester 3 under basic conditions is converted to compound 4.

Step-7 reaction is performed in a two-phase mixture comprising of an aqueous base, preferably aqueous sodium hydroxide solution and a water-immiscible organic aprotic solvent. Phase transfer catalyst facilitates the homogeneous reaction between aqueous layer and aprotic solvent used in step-7.

In one aspect, the obtained intermediate 4 is isolated as white crystalline solid by treatment with strong acidic resin followed by purification from a mixture of protic solvents, which further avoids the usage of freeze drier as reported in the prior art.

In an alternative method as described in scheme-4, compound 18b or 18c are isolated as a free base by using suitable organic base selected from the group comprising of pyridine, trimethylamine, leutidine, 1,4-diazabicyclo[2.2.2]octane (DABCO), 1,8-Diazabicyclo[5.4.0]undec-7-ene (DBU), 1,2,2,6,6-pentamethylpipiridine, 1,1,3,3-tetramethylguanidine, diisopropyl ethylamine (iPr$_2$Net), tributylamine (NBu$_3$), N,N-dicyclohexylmethylamine (Cy$_2$NMe) or the like. In one aspect, suitable organic base used is triethylamine.

Alternatively, treatment of free base of compound 18 i.e 18a or optionally its acid salts (18b or 18c) with 6-10 equivalents of chloroacetic acid or bromoacetic acid in the presence of aqueous sodium hydroxide at pH 10-12 generated compound 4 in good yields.

Finally, in step-9, treatment of intermediate 4 with strong acid resin followed by gadolinium (III) oxide in the presence of sodium hydroxide provided compound of formula 1.

In another aspect of the invention provided amorphous for of Gadolinium disodium (1) characterised by a powder X-ray diffraction pattern as shown in FIG. 1.

In another embodiment the invention provides a process for preparation of Gadoxetate disodium of formula 1 with greater than 99% purity comprising the steps of:
a) suspending compound of formula 4 in water and adjusting pH of the solution to 3.0 to 3.2 using acid resin;

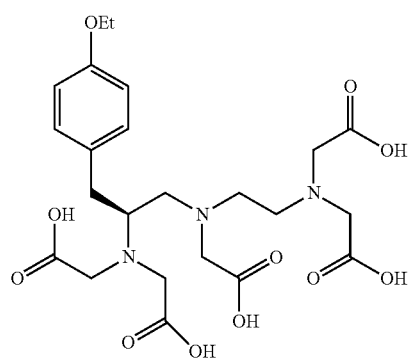

4 b) removing the resin and adding gadolinium oxide to the reaction mixture;
c) heating the reaction mixture for 4-5 hrs. at 85-90° C.;
d) filtering and adjusting pH to 6.5 to 7.0 using base;
e) treating with activated carbon at 40-45° C. and filtering through hyflo bed.

In the above process the acid resin used is selected from INDION 225H and 525H.

The base used is selected from the group comprising of potassium hydroxide, lithium hydroxide, sodium hydroxide, potassium carbonate and sodium carbonate.

In another aspect the invention provides novel intermediate compounds of formula 15 and formula 16, which are used in the synthesis of Gadoxetate disodium of formula 1.

In one embodiment the invention provides a compound (S)-tert-butyl 1-(4-ethoxyphenyl)-3-hydroxypropan-2-ylcarbamate of formula 15.

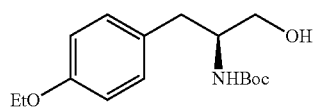

15

In one embodiment the invention provides a compound (S)-2-((tert-butoxycarbonyl)amino)-3-(4-ethoxyphenyl) propyl methanesulfonate of formula 16.

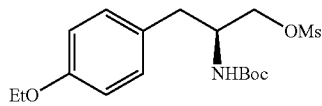

16

In another aspect the invention provides a process for the preparation of (S)-2,2'-(2-((2-(bis(carboxymethyl)amino)-3-(4-ethoxyphenyl)propyl)(carboxymethyl)amino)ethyl-azanediyl)diacetic acid of formula 4

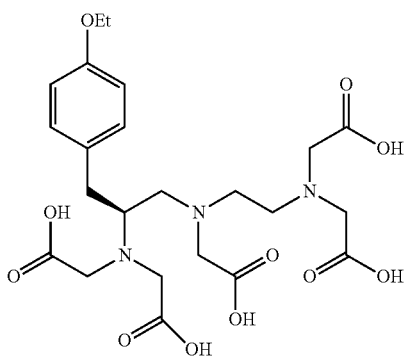

4 with greater than 99% purity comprising the steps of:
i. suspending compound 3 in methanol and aqueous sodium hydroxide;

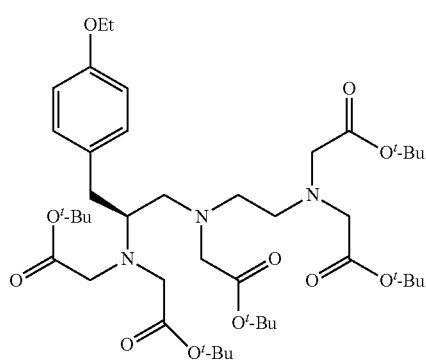

3 ii. refluxing the solution for 5-6 hrs;
iii. cooling to room temperature and adjusting pH to 6.5 to 7.0 by acidic resin;
iv. filtering and washing the solid with a mixture of methanol and isopropyl alcohol.

Definitions

The following terms shall have for the purpose of this application, including the claims appended here to, the respective meanings set forth below.

The term "alkylation reagent" used herein is selected from the group comprising ofdiethyl sulphate, ethyl iodide, ethyl bromide, ethyl chloride or the like The term "hydroxyl activating groups' used herein is selected from the group comprising of mesylates, tosylates, acetates, triflates or the like, most preferably methanesulfonyl chloride;

The term "organic base" used herein is selected from the group comprising pyridine, triethylamine, leutidine, 1,4-diazabicyclo[2.2.2]octane (DABCO), 1,8-Diazabicyclo[5.4.0]undec-7-ene (DBU), 1,2,2,6,6-pentamethylpipiridine, 1,1,3,3-tetramethylguanidine, N,N-Diisopropylethylamine (iPr$_2$Net), tri n-butyl amine (NBu$_3$), N,N-Dicyclohexylmethylamine (Cy$_2$NMe) or the like, most preferably triethylamine.

The term "base" used herein is selected from the group comprising of alkali hydroxides, alkoxides, alkali hydrides, or compounds such as amine derivatives, carbonates or the like, for example potassium hydroxide, lithium hydroxide, sodium hydroxide, potassium carbonate, sodium carbonate, lithium carbonate, alkoxides like sodium methoxide, sodium ethoxides, potassium tert.butoxide, sodium tert.butoxide, organic bases such as triethyl amine, pyridine, 4-Dimethylaminopyridine (DMAP), Sodium bis(trimethylsilyl)amide (NaHMDS), lithium bis(trimethylsilyl)amide (LiHMDS), Diisopropylamine (DIPA), pyrrolidine or the like.

The term 'aprotic solvent' used herein is selected from the group comprising of dichloromethane, chloroform, dichloroethane acetonitrile, dimethyl sulphoxide (DMSO), tetrahydrofuran (THF), dimethyl formamide (DMF), ethyl acetate, acetone, n-methyl pyrrolidine (NMP), dimethyl acetamide (DMA), diethyl ether, methyl tert-butyl ether (MTBE), toluene, cyclohexanes, hexanes, dioxanes or the like.

The term 'protic solvent' used herein is selected from the group comprising of alcohols like methanol, ethanol, isopropanol, n-propanol, n-butanol; water; formic acid, nitromethane, acetic acid or the like The term 'alcoholic solvent' used herein is selected from the group comprising of methanol, ethanol, n-propanol, n-butanol, isopropyl alcohol or the like.

The term solvent used herein is selected from the group comprising of aprotic, protic, water or mixtures thereof.

The term strong acid resin used herein is selected from the group comprising of INDION 225, 525H or the like.

The following examples further illustrate the present invention, but should not be construed in any way as to limit its scope.

Example-1

Preparation of (S)-2-((tert-butoxy carbonyl)amino)-3-(4-hydroxyphenyl)propanoic acid (13)

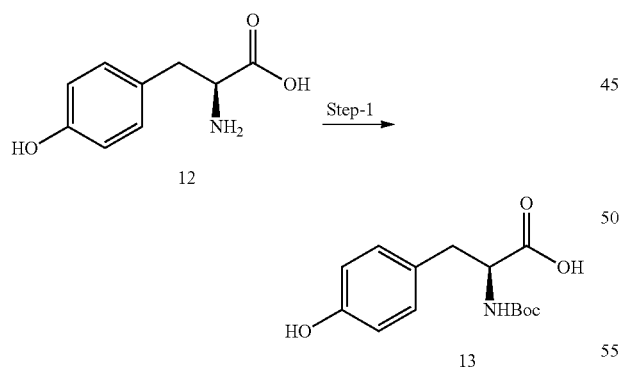

100 g of L-tyrosine 12 was suspended in THF: water (1:1, 2000 mL). 130 mL of trimethylamine was then added drop wise at 20-25° C. The reaction mixture was cooled to 0-5° C. and di-tert-butyl carbonate (132 g) was added drop wise over a period of 30 minutes. The reaction temperature was raised to 20-25° C. and suspension was stirred for 18-20 hrs. at 20-25° C. The resulting reaction mixture was concentrated and a mixture of ethyl acetate (1000 mL) and water (500 mL) was added. The aqueous phase was collected and adjusted to pH 3.0 to 4.0 using hydrochloric acid (1.0 M). The aqueous mixture was extracted with ethyl acetate (2000 mL). The combined organic layer was dried over magnesium sulphate, filtered and concentrated to give 144 g of the title compound 13 as pale yellow coloured liquid. Yield: 92%, Purity by HPLC: 95.34%

Example-2

Preparation of (S)-2-((tert-butoxy carbonyl)amino)-3-(4-hydroxyphenyl)propanoic acid (14)

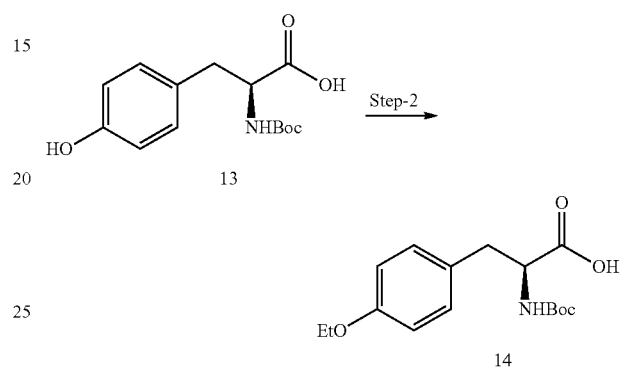

100 g of N-t-butoxy carbonyl-L-tyrosine 13 was dissolved in sodium hydroxide (4N, 300 mL) at 20-25° C. Diethyl sulphate (109.5 g) was added over a period of 20-30 min. The reaction mixture was stirred for 2-3 hr, and then it was cooled with ice-bath at 15-20° C. Then, ethyl acetate (600 mL) was added, followed by slow addition of hydrochloric acid (3 N, 600 mL) for 1.0 hr. The ethyl acetate layer was separated, and the aqueous layer was extracted with ethyl acetate (600 mL). The ethyl acetate layer was concentrated up to 200 ml volume, then cyclohexane (700 mL) was added. The reaction mixture was stirred in an ice-bath for 2-3 hr. The resultant white solid was filtered and washed with hexane (300 mL) in three portions. The solid was dried under vacuum below 50° C. to yield 85 g of the title compound 14. Yield: 78%, Purity by HPLC: 99.67%

Example-3

Preparation of (S)-tert-butyl(1-(4-ethoxyphenyl)-3-hydroxypropan-2-yl)carbamate (15)

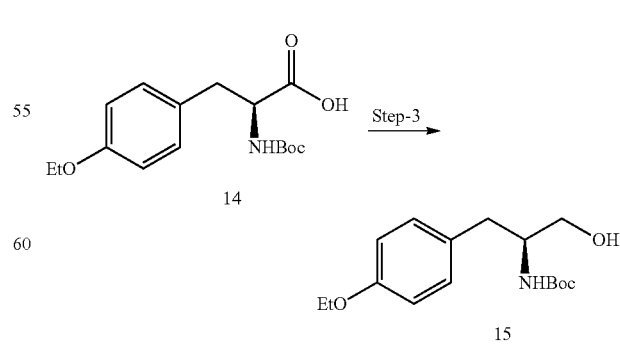

100 g of compound 14 was dissolved in dichloromethane (1000 ml) and cooled to 0-5° C., and 272 mL of triethylamine was added drop wise for 20-30 min followed by ethyl chloroformate (123 mL) at same temperature for 30-40 min. Then, reaction mass temperature was raised to 25-30° C. and stirred at same temperature for 2-3 hr. The reaction mixture was quenched with 500 mL of water and the dichloromethane layer was separated. The aqueous layer was extracted with dichloromethane (200 mL). The combined organic layer was dried over magnesium sulphate, filtered and concentrated under reduced pressure. The crude was dissolved in 500 ml of tetrahydrofuran and 3 equiv. of sodium borohydride was added in to the reaction mixture at 0-5° C. 300 mL of Methanol was added to the reaction mixture over a period of 5-6 h at 0-5° C. and the temperature was raised to room temperature. After completion of the reaction, the solvent was distilled completely and the crude product isolated and purified by recrystallization using ethyl acetate and cyclohexane to afford compound 15 as a solid. Yield: 60%, Purity by HPLC: 96.25%

Example-4

(Alternative procedure) Preparation of (S)-tert-butyl (1-(4-ethoxyphenyl)-3-hydroxypropan-2-yl)carbamate (15)

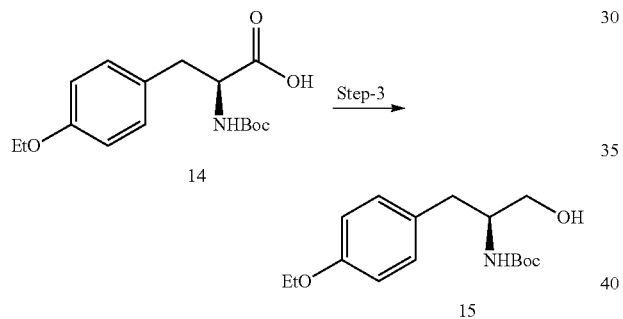

100 g of compound 14 was dissolved in 500 mL of dimethyl formamide and cooled to 0-5° C. To this 134 g of potassium carbonate and 68.8 g of methyl iodide were added and stirred for 30 min at 0-5° C. The temperature of the reaction mass was raised to 25-30° C. and stirred for 7-10 hrs at 25-30° C. On completion of the reaction, the reaction mass was cooled to 0-5° C. and 2000 mL of DM water was added and stirred for 2 hrs. The precipitated solid was filtered and washed with water. The obtained solid was charged with 7 V of tetrahydrofuran and cooled to 0-5° C. under nitrogen atmosphere. To this 0.29 g of sodium borohydride was added in lot wise followed by methanol for 3-4 hrs. at 0-5° C. The reaction mass was stirred for 60 minutes at 0-5° C. then the reaction mass temperature was raised slowly to 25-30° C. and maintained for 10-12 hrs. at 25-30° C. On completion of reaction, DM water was added and stirred for 1-2 hrs at 25-30° C. The solvent was distilled off completely and cooled to 15-20° C. The reaction mass was extracted with Ethyl acetate, then distilled off under vacuum. Cyclohexane was added to the crude and stirred for 2-3 hrs at 20-25° C. The precipitated solid was filtered and dried under vacuum below 50° C. Yield %: 70-75; Purity by HPLC: 96%

Example-5

Preparation of (S)-2-((tert-butoxy carbonyl)amino)-3-(4-ethoxyphenyl)propyl methane sulfonate (16)

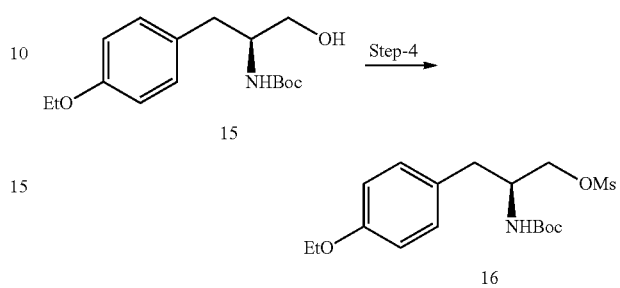

100 g of compound 15 was dissolved in dichloromethane (1000 mL) and cooled to 0-5° C., 143 mL of trimethylamine was added drop wise for 20-30 min then methane sulfonyl chloride (40 mL) was added at same temperature for 30-40 min. Then, temperature was raised to 25-30° C. and stirred for 2-3 hr. The reaction mixture was quenched with 300 mL of water and the dichloromethane layer was separated. The aqueous layer was extracted with dichloromethane (200 mL). The combined organic layer was dried over magnesium sulphate, filtered and concentrated to give 88 g of the title compound 16 as white coloured solid. Yield: 64%, Purity by HPLC: 95.12%

Example-6

Preparation of (S)-tert-butyl (1-((2-aminoethyl)amino)-3-(4-ethoxyphenyl)propan-2-yl)carbamate (17)

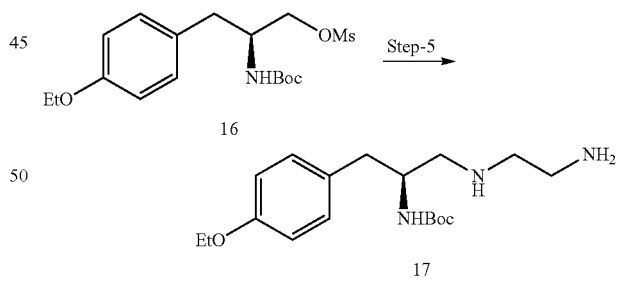

100 g of compound 16 was dissolved in tetrahydrofuran (600 mL), 446 mL of ethylenediamine was added at 20-25° C. The reaction mixture was stirred at 60-65° C. for 10-12 hr. After evaporation of the tetrahydrofuran and most of the excess ethylene diamine under reduced pressure, the mixture was diluted with 200 mL of water and extracted three times with 300 mL of ethyl acetate each. The combined organic extracts were washed with water, dried over sodium sulphate, and concentrated under vacuum to give 67 g of the title compound 17 as pale yellow coloured liquid. Yield: 72%; Purity by HPLC: 95%

Example-7

Preparation of (S)—N-1-(2-aminoethyl)-3-(4-ethoxyphenyl)propane-1,2-diamine trihydrochloride (18b)

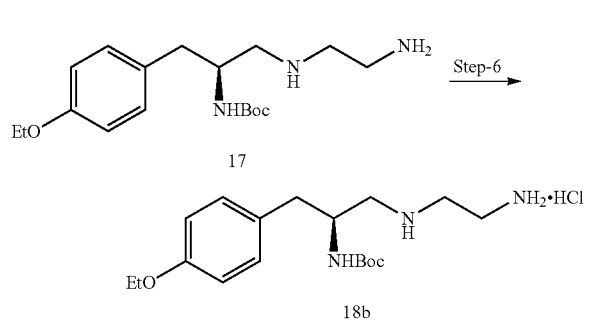

100 g of compound 17 was dissolved in 1,4-dioxane (450 mL), 200 mL of concentrated hydrochloric acid was added at 0-5° C. for 20-30 min. The reaction mixture was stirred for 6-8 hrs at 20-25° C. 450 mL of acetone was added and stirred for 1-2 hr at 20-25° C. The resultant white solid was filtered and washed with acetone (100 mL). The solid was dried under vacuum at 50-55° C. to give 70 g of the title compound 18b as white solid. Yield: 68%; Purity by HPLC: 99.62%

Example-8

Preparation of (S)—N1-(2-aminoethyl)-3-(4-ethoxyphenyl)propane-1,2-diamine dihydrochloride (18a)

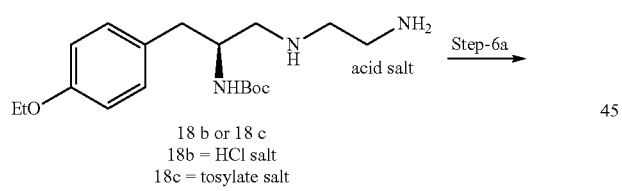

100 g of compound 18 was dissolved in dichloromethane (1000 mL), 143 mL of triethylamine was added at 20-25° C. for 20-30 min. The reaction mixture was stirred for 1-2 hrs at 20-25° C., 300 mL of dichloromethane was added and stirred at 20-25° C. for 1.0 hr. The resultant white solid was filtered and washed with dichloromethane (100 mL). The solid was dried under vacuum at 50-55° C. to give 62 g of the title compound 18a as white solid.

Yield: 95%; Purity by HPLC: 99.67%

Example-9

Preparation of (S)—N-1-(2-aminoethyl)-3-(4-ethoxyphenyl)propane-1,2-diamine tosylate (18c)

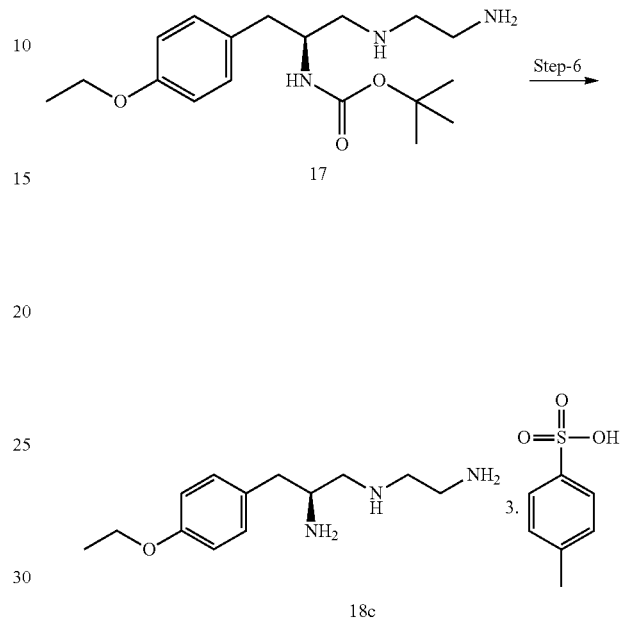

100 g of compound 17 was dissolved in tetrahydrofuran (1000 mL), 150 g of p-toluene sulphonic acid was added at 25-30° C. The reaction temperature was raised to 60-65° C. and stirred for 12 hrs. On completion of reaction 100 ml of tetrahydrofuran and methyl tert-butyl ether were added and stirred for 2-3 hrs at 65-70° C. The precipitated solid was filtered and washed with tetrahydrofuran. 5 volumes of isopropyl alcohol was added and stirred for 10 minutes at 25-30° C. The reaction mixture was heated for 60 minutes at 80-85° C. and cooled to 25-30° C. The reaction mass was maintained for 60 minutes at 25-30° C. and filtered under vacuum. The obtained solid was filtered and washed with a mixture of isopropyl alcohol and ethyl acetate to yield tosylate salt 18c. Yield: 68%; Purity by HPLC: 99.62%

Example-10

Preparation of (S)-di-tert-butyl 2,2'-((2-((2-(bis(2-(tert-butoxy)-2-oxoethyl)amino)-3-(4-ethoxyphenyl)propyl)(2-(tert-butoxy)-2-oxoethyl)amino)ethyl)azanediyl)diacetate (3)

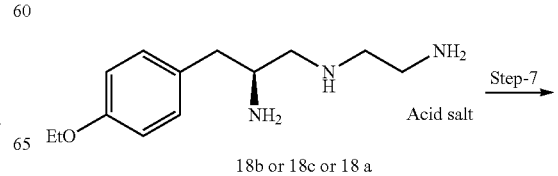

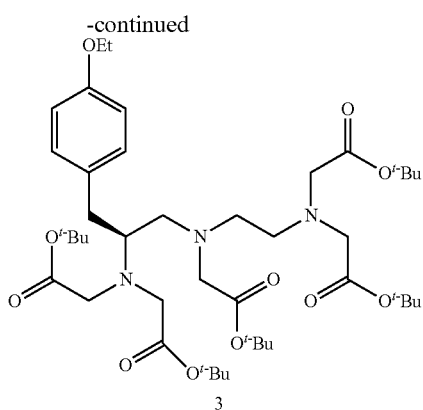

3

100 g of compound 18b or 18c or 18a was suspended in 1500 mL of tetrahydrofuran and 3 V of water at 25-30° C. After addition of 340 g of potassium carbonate and 200 mL of water, 363 mL of tert-butyl bromoacetate was added drop wise into the reaction mixture at 25-30° C. The resultant reaction mass was stirred for 20-24 hr at 60-65° C. The resulting reaction mass was cooled to room temperature, solid was filtered off After evaporation of the tetrahydrofuran, mixture was extracted three times with 300 mL of dichloromethane each. The combined organic extracts were washed with water, dried over sodium sulphate, and concentrated under vacuum to give 163 g of the title compound 3 as pale yellow coloured liquid. Yield: 69%; Purity by HPLC: 96%

Example-11

(Alternative Procedure) Preparation of (S)-di-tert-butyl 2,2'-((2-((2-(bis(2-(tert-butoxy)-2-oxoethyl) amino)-3-(4-ethoxyphenyl)propyl)(2-(tert-butoxy)-2-oxoethyl)amino)ethyl)azanediyl)diacetate (3)

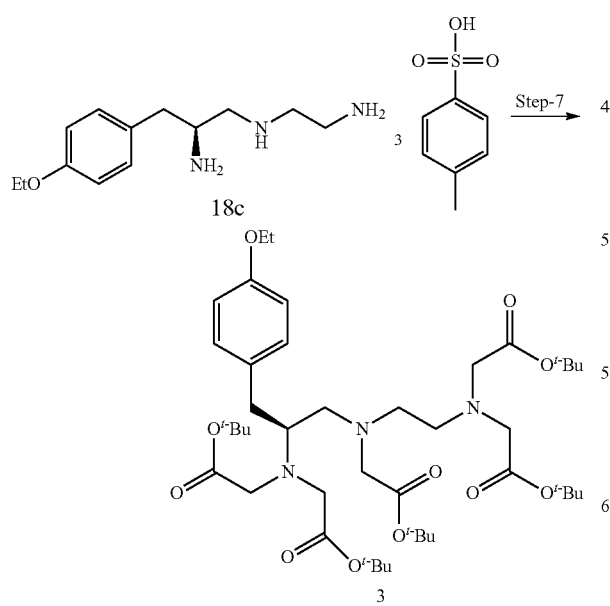

363 mL of tert-butyl bromoacetate was added drop wise to a mixture of toluene (500 mL), water, (500 mL) compound 18b or 18c (100 g), potassium carbonate (200 g), tetrabutylammonium bromide (8 g), potassium iodide (8 g) at 80-90° C. On completion of addition, reaction was maintained for 15-18 hrs, then reaction mass was cooled to room temperature, organic and aqueous layers were separated. Organic layer was washed with dilute hydrochloric acid (2×50 mL of 1N aqueous hydrochloric acid), followed by aqueous sodium bicarbonate solution (2×50 mL of 10% aqueous sodium bicarbonate solution). The organic layer was dried over sodium sulphate to get the title compound 3 as pale yellow coloured liquid. Yield: 88%; Purity by HPLC: 97%

Example-12

Preparation of (S)-2,2'-((2-((2-(bis(carboxymethyl) amino)-3-(4-ethoxyphenyl)propyl)(carboxymethyl) amino)ethyl)azanediyl)diacetic acid (4)

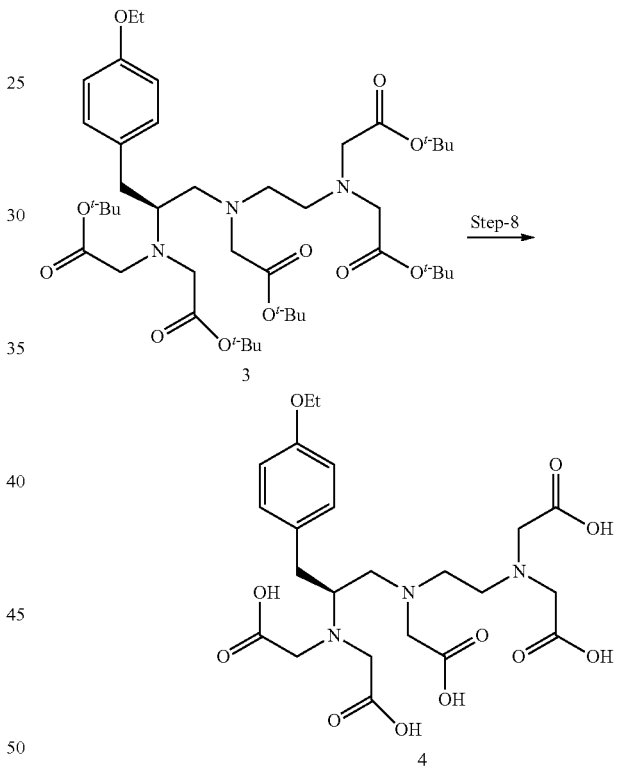

100 g of compound 3 was suspended in 750 mL of methanol, 49 g of sodium hydroxide was added in 100 ml of water at 25-30° C. The solution was refluxed for 5-6 hr and stirred at room temperature for 10-12 hrs. The pH of the aqueous layer was adjusted to 6.5 to 7.0 by using strong acidic resin (i.e., INDION 225H or 525H). The reaction mass was then filtered and distilled off the filtrate at 45-50° C. To the crude, methanol followed by isopropyl alcohol were added and distilled under vacuum. Further, methanol was added and cooled to 25-30° C., then isopropyl alcohol was added and stirred for 2-3 hrs. at 25-30° C. The precipitated solid was filtered and charged with 800 mL of methanol. Then the reaction mixture was heated to 60-65° C. and stirred for 2-3 hrs at 60-65° C. The obtained solid was charged with 9:1 ratio of methanol and isopropyl alcohol mixture and heated to 60-65° C. The solid was filtered and washed with mixture of methanol and isopropyl alcohol to give 32 g of the title compound 4 as white solid. Yield: 50%; Purity by HPLC: 99%

Example-13

Preparation of (S)-2,2'-((2-((2-(bis(carboxymethyl) amino)-3-(4-ethoxyphenyl)propyl)(carboxymethyl) amino)ethyl)azanediyl)diacetic acid (4)

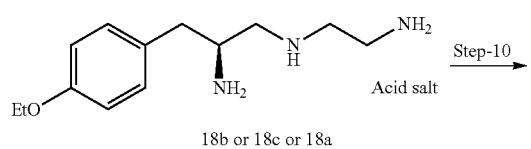

18b or 18c or 18a

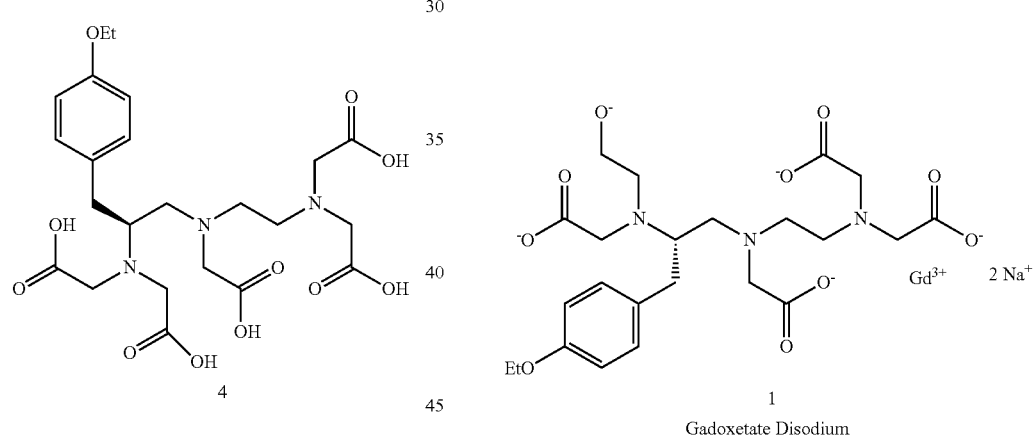

100 g of compound 18b or 18c or 18a was suspended in 500 mL of water and cooled to 0-5° C. Then, 163 g of chloroacetic acid in 100 mL of water was added at 0-5° C. drop wise for 20-30 min. Then, the pH of the reaction mass was adjusted to 10-10.5 by using 60% sodium hydroxide solution at 0-5° C. The solution was refluxed for 15-17 hrs and cooled to room temperature. Then, the pH of the aqueous layer was adjusted to 6.5 to 7.0 by using strong acidic resin (i.e., INDION 225H or 525H). The resulting aqueous layer passed through 500 mL of INDION 225H or 525H and concentrated under vacuum. The obtained solid was charged with 800 ml of methanol. The reaction mixture was heated for 2-3 hrs at 60-65° C. then filtered under vacuum. To the solid, 9:1 ratio of methanol and isopropyl alcohol mixture was charged and heated to 60-65° C. The solid was filtered and washed with mixture of methanol and isopropyl alcohol to give 64 g of the title compound 4 as white solid. Yield: 42%; Purity by HPLC: 99.8%

Example-14

Preparation of Gadoxetate disodium (1)

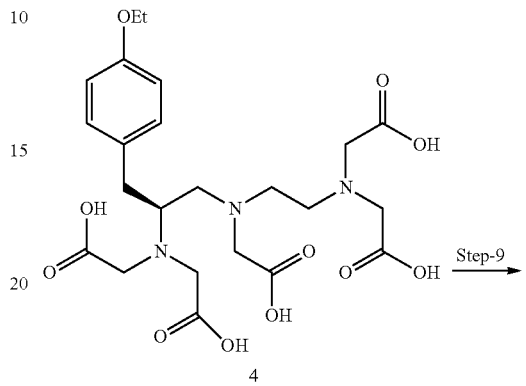

100 g of compound 4 was suspended in 600 mL of water and pH of the mixture was adjusted to 3.0 to 3.2 using acid resin. Then the resin was filtered and gadolinium oxide was charged to the filtrate at 25-30° C. The reaction mass temperature was raised to 85-90° C. and stirred for 4-5 hrs. The reaction mass was filtered and pH adjusted to 6.5 to 7.0 using aqueous sodium hydroxide solution, then treated with activated carbon and heated to 40-45° C. The obtained reaction mass was filtered through hyflo bed and checked for gadolinium content. The resultant solution was concentrated under vacuum to give 108 g of the Gadoxetate disodium (1) as white solid. Yield: 70%; Purity by HPLC: 99.9%

We claim:

1. A process for the preparation of a gadolinium complex of (4S)-4-(4-Ethoxybenzyl)-3,6,9-tris(carboxylatomethyl)-3,6,9-triazaundecanedioic acid disodium (Gadoxetate disodium) of formula 1

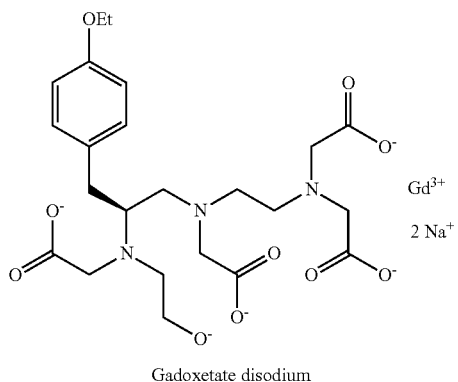

Gadoxetate disodium comprising the steps of:

i) protecting the amino group of L-tyrosine of formula 12 with di-tert-butyl dicarbonate (Boc₂O) in the presence of a base to get boc-protected L-tyrosine of formula 13;

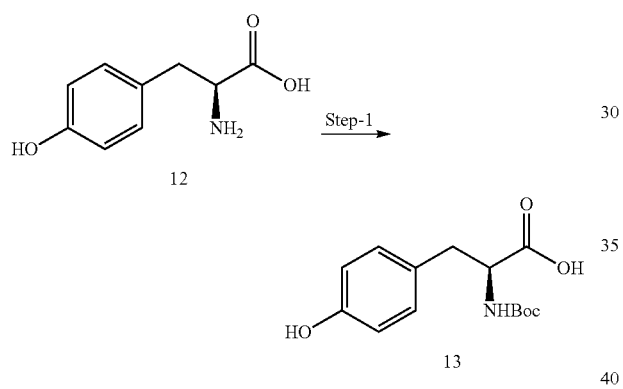

ii) alkylating the Boc-protected L-tyrosine of formula 13 with diethyl sulfate in a solvent to obtain a compound of formula 14;

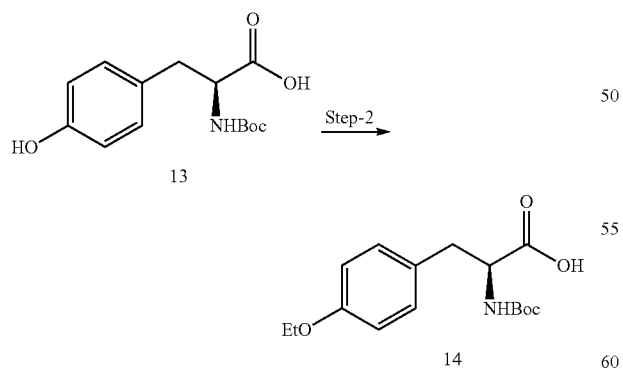

iii) converting the compound of formula 14 in to anhydride or ester in situ by reacting with a reagent followed by reduction with a reducing agent to obtain (S)-tert-butyl (1-(4-ethoxyphenyl)-3-hydroxypropan-2-yl) carbamate of formula 15;

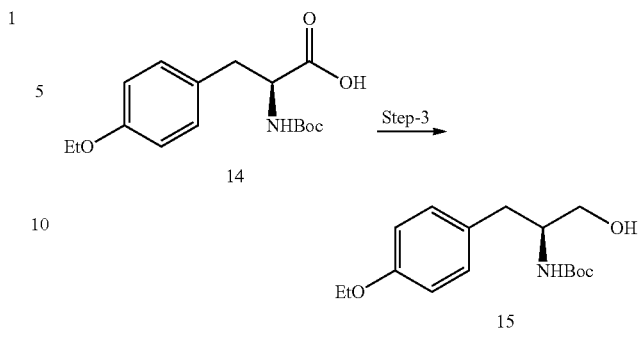

iv) protecting the hydroxyl group in the (S)-tert-butyl (1-(4-ethoxyphenyl)-3-hydroxypropan-2-yl) carbamate of formula 15 with methanesulfonyl chloride in the presence of a base to obtain (S)-2-((tert-butoxycarbonyl)amino)-3-(4-ethoxyphenyl) propyl methanesulfonate of formula 16;

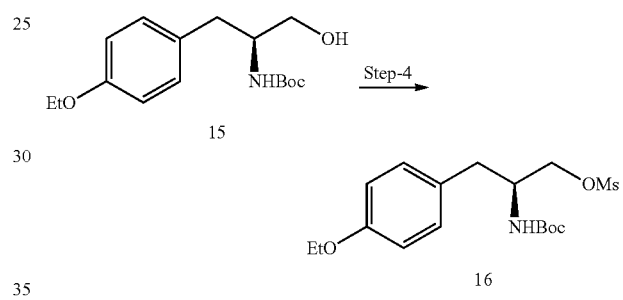

v) condensing the (S)-2-((tert-butoxy carbonyl) amino)-3-(4-ethoxyphenyl) propyl methanesulfonate of formula 16 with ethylenediamine in a solvent to obtain (S)-tert-butyl (1-((2-aminoethyl) amino)-3-(4-ethoxyphenyl)propan-2-yl)carbamate of formula 17;

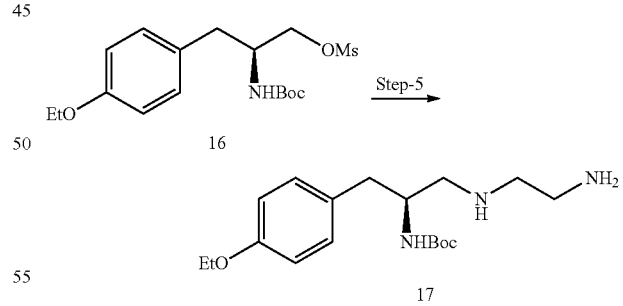

vi) deprotecting the amino protecting group from the (S)-tert-butyl (1-((2-aminoethyl) amino)-3-(4-ethoxyphenyl) propan-2-yl)carbamate of formula 17 in the presence of an acid to obtain (S)-N1-(2-aminoethyl)-3-(4-ethoxyphenyl)propane-1,2-diamine acid salt of formula 18b or 18c, which optionally, is further converted in to a free base that is a compound of formula 18a, in situ by reaction with a base;

35

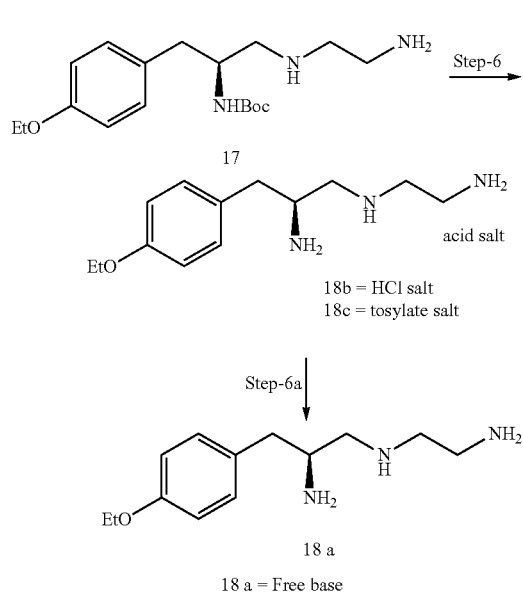

vii) alkylating the (S)-N1-(2-aminoethyl)-3-(4-ethoxyphenyl) propane-1,2-diamine acid salt of formula 18b or 18c or the free base that is the compound of formula 18a with tertiary butyl bromoacetate in the presence of potassium carbonate to provide (S)-tert-butyl 2,2'-(2-((2-(bis(2-tert-butoxy-2-oxoethyl) amino)-3-(4-ethoxyphenyl)propyl) (2-tert-butoxy-2-oxoethyl)amino) ethyl azanediyl) diacetate of formula 3;

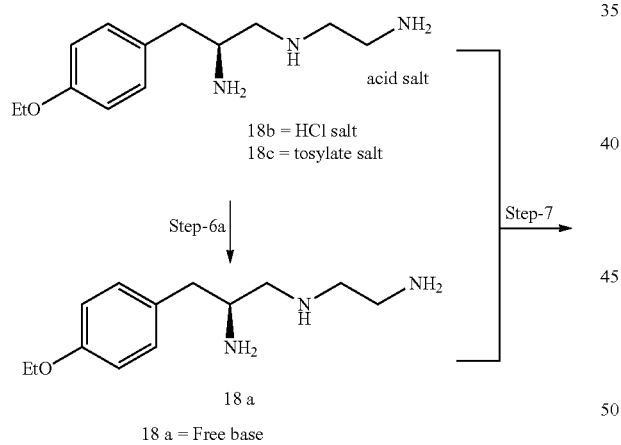

36 viii) deprotecting the tertiary butyl group of the (S)-tert-butyl 2,2'-(2-((2-(bis(2-tert-butoxy-2-oxoethyl)amino)-3-(4-ethoxyphenyl)propyl) (2-tert-butoxy-2-oxoethyl)amino) ethyl azanediyl) diacetate of formula 3 with aqueous sodium hydroxide to obtain (S)-2,2'-((2-((2-(bis(carboxymethyl)amino)-3-(4-ethoxyphenyl)propyl) (carboxymethyl) amino)ethyl) azanediyl)diacetic acid of formula 4;

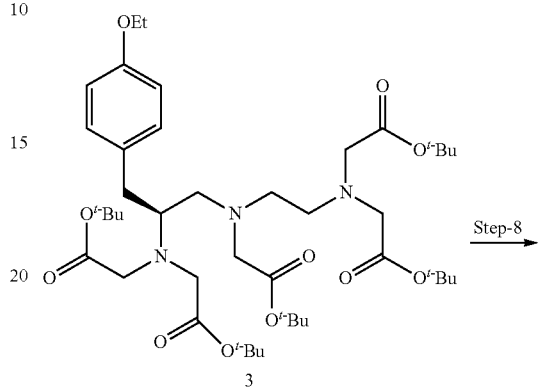

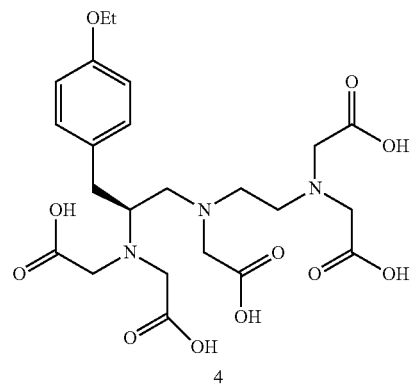

ix) converting the (S)-2,2'-((2-((2-(bis(carboxymethyl) amino)-3-(4-ethoxyphenyl) propyl) (carboxymethyl) amino)ethyl)azanediyl)diacetic acid of formula 4 to Gadolinium salt by treating with Gadolinium(III) oxide in the presence of sodium hydroxide to obtain the Gadoxetate Disodium of formula 1

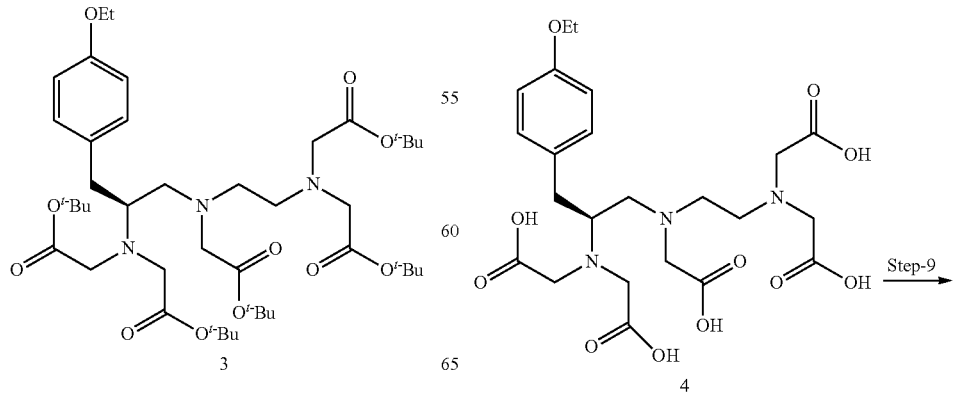

-continued

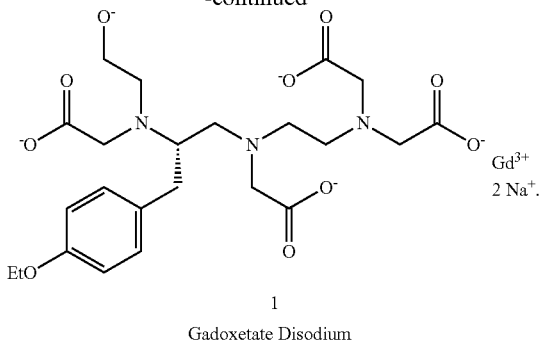

1

Gadoxetate Disodium

2. The process as claimed in claim 1, wherein the reducing agent of step-iii is selected from the group consisting of sodium cyanoborohydride, sodium triacetoxy boron hydride, lithium aluminium hydride and sodium borohydride.

3. The process as claimed in claim 1, wherein in step-iv the hydroxyl group of the (S)-tert-butyl (1-(4-ethoxyphenyl)-3-hydroxypropan-2-yl) carbamate of formula 15 is activated with a hydroxyl activating group, wherein the hydroxyl activating group is selected from the group consisting of mesylates, tosylates, acetates and triflates.

4. The process as claimed in claim 1, wherein the acid of step-vi is p-toluene sulphonic acid or hydrochloric acid.

5. The process as claimed in claim 1, wherein the solvent of step-ii is selected from the group consisting of an aprotic solvent, a protic solvent, water and mixtures thereof.

6. The process as claimed in claim 5, wherein the solvent is an aprotic solvent, and the aprotic solvent is dichloromethane, chloroform, dichloroethane acetonitrile, dimethyl sulphoxide (DMSO), tetrahydrofuran (THF), dimethyl formamide (DMF), ethyl acetate, acetone, n-methyl pyrrolidine (NMP), dimethyl acetamide (DMA), diethyl ether, methyl tertbutyl ether (MTBE), toluene, cyclohexanes, hexanes or dioxanes.

7. The process as claimed in claim 5, wherein the solvent is a protic solvent, and the protic solvent is methanol, ethanol, isopropanol, n-propanol, n-butanol, water, formic acid, nitromethane or acetic acid.

8. The process as claimed in claim 1, wherein the reagent of step-iii is ethylchloroformate or methyl iodide.

9. The process as claimed in claim 1, wherein the solvent of step-v is selected from the group consisting of aromatic hydrocarbon solvents consisting of toluene and xylene; amide solvents consisting of N,N-dimethylformamide; sulphoxide solvents consisting of dimethylsufoxide; and ethers solvents consisting of tetrahydrofuran and 1,4-dioxane.

10. The process as claimed in claim 9, wherein the solvent is tetrahydrofuran.

11. The process as claimed in claim 1, wherein the base of step-vi is selected from the group consisting of alkali hydroxides consisting of potassium hydroxide, lithium hydroxide, and sodium hydroxide; alkali hydrides; amine derivatives; carbonates consisting of potassium carbonate, sodium carbonate, and lithium carbonate; alkoxides consisting of sodium methoxide, sodium ethoxides, potassium tertbutoxide, and sodium tertbutoxide; and organic bases consisting of triethyl amine, pyridine, 4-Dimethylaminopyridine (DMAP), Sodium bis(trimethylsilyl)amide (NaHMDS), lithium bis(trimethylsilyl)amide (LiHMDS), Diisopropylamine (DIPA) and pyrrolidine.

12. The process as claimed in claim 11, wherein the base is triethylamine.

* * * * *